US008148152B2

(12) United States Patent
Kolossov et al.

(10) Patent No.: US 8,148,152 B2
(45) Date of Patent: Apr. 3, 2012

(54) METHOD FOR THE PREPARATION OF EMBRYOID BODIES (EBS) AND USES THEREOF

(75) Inventors: Eugen Kolossov, Köln (DE); Ralf Kettenhofen, Bonn (DE); Isabella Kopp, Köln (DE); Heribert Bohlen, Köln (DE); Silke Schwengberg, Düren (DE)

(73) Assignee: Axiogenesis AG, Cologne (DE)

( * ) Notice: Subject to any disclaimer, the term of this patent is extended or adjusted under 35 U.S.C. 154(b) by 216 days.

(21) Appl. No.: 10/594,188

(22) PCT Filed: Jul. 8, 2004

(86) PCT No.: PCT/EP2004/007530
§ 371 (c)(1),
(2), (4) Date: Jun. 21, 2007

(87) PCT Pub. No.: WO2005/005621
PCT Pub. Date: Jan. 20, 2005

(65) Prior Publication Data
US 2008/0019952 A1 Jan. 24, 2008

(30) Foreign Application Priority Data
Jul. 8, 2003 (EP) .................................. 03015401

(51) Int. Cl.
*C12N 5/00* (2006.01)
*C12N 5/02* (2006.01)
*C12N 15/63* (2006.01)
*C07H 21/02* (2006.01)
*C07H 21/04* (2006.01)

(52) U.S. Cl. ........ 435/383; 435/325; 435/375; 435/377; 435/455; 536/23.1; 536/24.1

(58) Field of Classification Search .................. 435/325, 435/375, 377, 383, 455; 536/23.1, 24.1
See application file for complete search history.

(56) References Cited

U.S. PATENT DOCUMENTS

| 6,602,711 B1 * | 8/2003 | Thomson et al. ............. 435/378 |
| 7,105,344 B2 | 9/2006 | Hescheler |
| 2003/0119107 A1 | 6/2003 | Dang et al. |
| 2004/0096432 A1 | 5/2004 | Fleischmann et al. |
| 2006/0168665 A1 | 7/2006 | Hescheler |
| 2007/0258948 A1 | 11/2007 | Kolossov et al. |

FOREIGN PATENT DOCUMENTS

WO    WO 01/62899 A2    8/2001

OTHER PUBLICATIONS

Benbenisty, Nissim, 2002 (US 20020146678 A1).*
Kurosawa, H., 2007, Journal of Bioscience and Bioengineering, vol. 5, p. 389-398.*
Dang et al., 2002, Biotechnol Bioeng, vol. 78, p. 442-453.*
Yan et al., Feb. 2003, US 20030027331 A1.*
Nguyen et al., 2010, Advanced Drug Delivery Reviews xxx, p. 1-12.*
Kehat, I., et al., "Human embryonic stem cells can differentiate into mycytes with structural and functional properties of cardiomyocytes," *J. Clin. Invest. 108*:407-414, American Society for Clinical Investigation (2001).
Meyer, N., et al., "A fluorescent reporter gene as a marker for ventricular specification in ES-derived cardiac cells," *FEBS Lett. 478*:151-158, Elsevier Science B.V. (2000).
Hidaka, K, et al., "Chamber-specific differentiation of Nkx2.5-positive cardiac precursor cells from murine embryonic stem cells," *FASEB J. 17*:740-742, The Federation of American Societies for Experimental Biology (Apr. 2003).
First Office Action for European Patent Application No. 04 740 822.4, dated Apr. 26, 2006.
International Search Report for International Application No. PCT/EP2004/007530, mailed on Jan. 19, 2005, European Patent Office, Netherlands.
U.S. Appl. No. 11/547,871, U.S. National Phase of PCT/EP05/03662, Int'l Filing Date Apr. 7, 2005, § 371 Date Sep. 28, 2007, Not Yet Published.
U.S. Appl. No. 10/594,177, U.S. National Phase of PCT/EP04/07529, Int'l Filing Date Jul. 8, 2004, Not Yet Published.
U.S. Appl. No. 11/596,262, U.S. National Phase of PCT/EP05/05087, Int'l Filing Date May 11, 2005, § 371 Date Aug. 29, 2007, Not Yet Published.
Bongso, A., et al., "Isolation and culture of inner cell mass cells from human blastocysts," *Human Reproduction 9*:2110-2117, Oxford University Press (1994).
Reubinoff, B.E., et al., "Embryonic stem cell lines from human blastocysts: somatic differentiation in vitro," *Nature Biotechnology 18*:399-404, Nature Publishing Group (2000).
NIH Human Embryonic Stem Cell registry, On-Line Publication, http://escr.ih.gov/ , retrieved May 13, 2003.
"Common position (EC) No. 19/98," Official Journal of the European Communities, pp. C110/17 to C110/34, Apr. 8, 1998.

(Continued)

*Primary Examiner* — Shin-Lin Chen
(74) *Attorney, Agent, or Firm* — Fanelli Haag PLLC

(57) ABSTRACT

Provided are means and methods for producing embryoid bodies (EBs) from multi- or pluripotent cells. In particular, a method of generating embryoid bodies (EBs) is described comprising agitation of a liquid suspension culture of multi- or pluripotent cells in a container until generation of cell aggregates, optionally diluting the suspension, and further agitation of the suspension until formation of EBs. Furthermore, the present invention relates to the use of the novel culturing method and EBs obtained thereby for a variety of applications including genomics, diagnostic assays, teratogenic/embryotoxicological and pharmacological assays as well as for the provision of tissue grafts.

48 Claims, 6 Drawing Sheets

OTHER PUBLICATIONS

Directive 98/44/EC of the European Parliament and of the Council, Official Journal of the European Communities, pp. L213/13 to L213/21, Jul. 30, 1998.

European Patent Office: Statement by the European Patent Office concerning the Resolution of the European Parliament of Oct. 4, 2001 on the patenting of BRCA1 and BRCA2 ("breast cancer") genes, pp. 1 to 5, Oct. 17, 2001.

Technical Board of Appeal 3.3.4: "Decision T356/93-3.3.4", Official Journal EPO 8:545-585, Aug. 1995.

Enlarged Board of Appeal: "Decision G1/98," Official Journal EPO, pp. 111-141, Mar. 2000.

Opposition Division: "Interlocutory decision in Opposition proceedings of file 94 913 174.2," pp. 1-29, Jul. 21, 2003.

Opposition Division: "Interlocutory decision in Opposition proceedings of file 85 304 490.7," pp. 1-29, Jan. 16, 2003.

Office Communication for European Application No. 04 740 822.4, mailed on Jun. 10, 2008, European Patent Office, Munich, Germany.

Maltsev, V.A., et al., "Cardiomyocytes Differentiated In Vitro From Embryonic Stem Cells Developmentally Express Cardiac-Specific Genes and Ionic Currents," *Circulation Research* 75:233-244, American Heart Association, Inc. (1994).

Wartenberg, M. et al., "The Embryoid Body as a Novel In Vitro Assay System for Antiangiogenic Agents," *Laboratory Investigation* 78:1301-1314, The United States and Canadian Academy of Pathology, Inc. (1998).

Wartenberg, M., et al., "Tumor-induced angiogenesis studied in confrontation cultures of multicellular tumor spheroids and embryoid bodies grown from pluripotent embryonic stem cells," *The FASEB Journal* 15:995-1005, The Federation of American Societies for Experimental Biology (2001).

Office Action issued Mar. 10, 2009 in corresponding Japanese Application No. 2006-518153.

English translation of Office Action issued Mar. 10, 2009 in corresponding Japanese Application No. 2006-518153.

Office Action mailed Jul. 8, 2009, in corresponding Australian Application No. 2004256209, Axiogenesis AG., filed Jul. 8, 2004.

* cited by examiner

METHOD FOR THE PREPARATION OF EMBRYOID BODIES (EBS) AND USES THEREOF

FIELD OF THE INVENTION

The present invention relates to a method for producing embryoid bodies (EBs) from multi- or pluripotent cells. In particular, the instant invention concerns a method of generating embryoid bodies (EBs) comprising agitation of a liquid suspension culture of multi- or pluripotent cells in a container until generation of cell aggregates, optionally diluting the suspension, and further agitation of the suspension until formation of EBs. Furthermore, the present invention relates to the use of the method and EBs so obtained for a variety of applications including, but not limited to "loss of function" assays with ES cells containing homozygous mutations of specific genes, "gain of function" assays with embryonic stem (ES) cells overexpressing exogenous genes, developmental analysis of teratogenic/embryotoxic compounds in vitro, pharmacological assays and the establishment of model systems for pathological cell functions, and application of differentiation and growth factors for induction of selectively differentiated cells which can be used as a source for tissue grafts.

BACKGROUND ART

Precursor cells have become a central interest in medical research. On the one hand, precursors can replace cells that are senescent or damaged by injury or disease, and on the other hand, these cells represent an ideal model for studying development and differentiation and the factors influencing these processes. Employing conventional cell lines for these studies has the disadvantage that individual cell lines may not be fully representative of the complex biology of an intact organism. Moreover, even repeating the tests in multiple cell lines does not reproduce or account for the complex interactions among cells and tissue that occur in an organism.

Efforts have been made for a couple of years to employ permanent cultures of totipotent/pluripotent embryonic stem (ES) cells for the detection of embryotoxic and mutagenic substances and for the preparation of tissue grafts. ES cells can differentiate in vitro in embryo-like aggregates, so-called embryoid bodies (EBs), derivatives of all three germ layers, i.e. mesoderm, ectoderm and endoderm. Thus, embryoid bodies are particularly suited for teratogenic/embryotoxicological studies as well as identification of cell type and tissue promoting factors, and as precursors for implant tissue for the treatment of damaged organs such as infarcted heart. Several protocols for the in vitro production of EBs have been described.

For example, WO02/051987 describes a protocol to obtain embryoid bodies in which the manufacturing takes place preferably with the "hanging drop" method or by methylcellulose culture (Wobus et al., Differentiation 48 (1991), 172-182).

Alternatively to this, spinner flasks (stirring cultures) are described as culture method. Therefore, the undifferentiated ES cells are introduced into stirring cultures and are mixed permanently according to an established procedure. Therefore, 10 million ES cells are introduced into 150 ml medium with 20% FCS and are stirred constantly with the rate of 20 rpm, wherein the direction of the stirring motion is changed regularly. 24 hours after introduction of the ES cells an extra 100 ml medium with serum is added and thereupon 100-150 ml of the medium is exchanged every day (Wartenberg et al., FASEB J. 15 (2001), 995-1005). Under these culture conditions large amounts of ES cell-derived cells, i.e. cardiomyocytes, endothelial cells, neurons etc., depending on the composition of the medium, may be obtained. The cells are selected by means of the resistance gene either still within the stirring culture or after plating, respectively. Recently, international application WO03/004626 described a method for generating large numbers of embryonic stem (ES) cell-derived tissue, wherein the guiding design is preventing EB aggregation by encapsulation of individual or multiple ES cells, for example in the form of agarose microdrops. Using this measure, a high EB efficiency has been reported in so-called encapsulated stirred culture. However, all of those methods are cumbersome and/or do not provide sufficient amounts of embryoid bodies suitable for example for high throughput screening (HTS) assays.

Thus, there remains a need for reliable, easy and cost-effective methods which are capable of providing EBs in sufficient quality and quantity. The solution to this technical problem is achieved by providing the embodiments characterized in the claims, and described further below.

SUMMARY OF THE INVENTION

The present invention relates to a method for producing embryoid bodies (EBs) from multi- or pluripotent cells comprising
(a) agitation of a liquid suspension culture of multi- or pluripotent cells in a container at a concentration of about 0.1 to $5 \times 10^6$ cells/ml until generation of cell aggregates; and
(b) optionally diluting the suspension; and further agitation of the suspension until formation of EBs.

The present invention also concerns the embryoid bodies obtained by the described method of the present invention as well as the differentiated cell or tissue derived from such embryoid bodies, in particular cardiomyocytes.

Furthermore, the present invention relates to the use of the method, embryoid bodies, cells and tissue of the present invention for "loss of function" assays of specific genes, "gain of function assays" of exogenous genes, developmental analysis of teratogenic/embryotoxic compounds, pharmacological assays, microarray systems, establishment of model systems for pathological cell functions, and application of differentiation and growth factors for induction of selectively differentiated cells or as a source for tissue grafts.

In addition, the instant invention relates to a kit for use in a method of the invention comprising culture media components, selectable markers, reference samples, microarrays, vectors, probes, containers, multi- or pluripotent cells.

Moreover, the present invention is directed to the use of cell containers, devices for agitation and/or culturing cells, culture media and components thereof, multi- or pluripotent cells, vectors, and microarrays for a method of the present invention.

In particular, the present invention relates to test systems to identify substances that influence the differentiation of cells into certain cell types. Therefore, the present invention provides a method for obtaining and/or profiling a modulator of cell differentiation. This method comprises contacting a test sample containing EBs obtained by the method of the present invention with the substance to be tested; and then determining the effect of the test substance on the EBs or on the amount of the reporter gene product or activity compared to a control sample. The EBs production and test system provided by the present invention is useful for drug screening purposes.

Other embodiments of the invention will be apparent from the description that follows.

*=$p<0.05$; =$p<0.01$;*=$p<0.002$.

Figure 6:
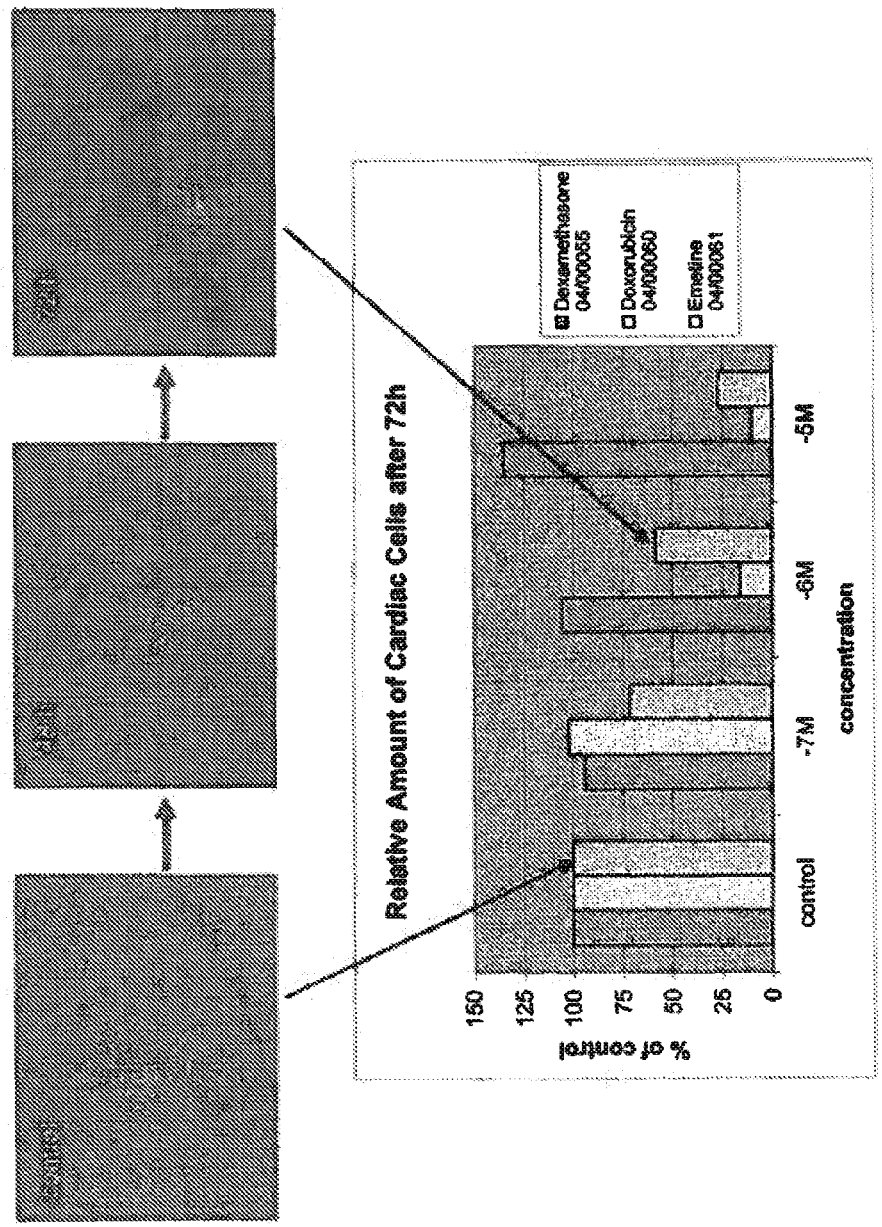

FIG. 6: Identification of cardiotoxic compounds. EBs were generated and cardiac cells were differentiated as described in Example 3. On day 14, EBs were treated with test compounds with known cardiotoxic potential as indicated in the figure. Photomicrographs were taken before treatment and 8 and 72 hours after treatment (green fluorescence represented by light-grey areas, total magnification 200×). Fluorescent areas representing cardiac cells were measured and calculated as described in Example 4.

DEFINITIONS

For the purposes of this description, the term "stem cell" can refer to either stem cell or germ cell, for example embryonic stem (ES) and germ (EG) cell, respectively. Minimally, a stem cell has the ability to proliferate and form cells of more than one different phenotype, and is also capable of self-renewal, either as part of the same culture, or when cultured under different conditions. Embryonic stem cells are also typically telomerase-positive and OCT-4 positive. Telomerase activity can be determined using TRAP activity assay (Kim et al., Science 266 (1997), 2011), using a commercially available kit (TRAPeze® XK Telomerase Detection Kit, Cat. s7707; Intergen Co., Purchase N.Y.; or TeloTAGGG™ Telomerase PCR ELISAplus, Cat. 2,013,89; Roche Diagnostics, Indianapolis). hTERT expression can also be evaluated at the mRNA level by RT-PCR. The LightCycler TeloT-AGGG™ hTERT quantification kit (Cat. 3,012,344; Roche Diagnostics) is available commercially for research purposes.

In accordance with the present invention, the term embryonic stem (ES) cell includes any multi- or pluripotent stem cell derived from pre-embryonic, embryonic or fetal tissue at any time after fertilization, and have the characteristic of being capable under appropriate conditions of producing progeny of several different cell types that are derivatives of all of the three germinal layers (endoderm, mesoderm and ectoderm), according to a standard art-accepted test, such as the ability to form a teratoma in 8-12 week old SCID mice.

"Embryonic germ cells" or "EG cells" are cells derived from primordial germ cells. The term "embryonic germ cell" is used to describe cells of the present invention that exhibit an embryonic pluripotent cell phenotype. The terms "human embryonic germ cell (EG)" or "embryonic germ cell" can be used interchangeably herein to describe mammalian, preferably human cells, or cell lines thereof, of the present invention that exhibit a pluripotent embryonic stem cell phenotype as defined herein. Thus, EG cells are capable of differentiation into cells of ectodermal, endodermal and mesodermal germ layers. EG cells can also be characterized by the presence or absence of markers associated with specific epitope sites identified by the binding of particular antibodies and the absence of certain markers as identified by the lack of binding of certain antibodies.

"Pluripotent" refers to cells that retain the developmental potential to differentiate into a wide range of cell lineages including the germ line. The terms "embryonic stem cell phenotype" and "embryonic stem-like cell" also are used interchangeably herein to describe cells that are undifferentiated and thus are pluripotent cells.

Included in the definition of ES cells are embryonic cells of various types, exemplified by human embryonic stem cells, described by Thomson et al. (Science 282 (1998), 1145); embryonic stem cells from other primates, such as rhesus stem cells (Thomson et al., Proc. Natl. Acad. Sci. USA 92 (1995), 7844), marmoset stem cells (Thomson et al., Biol. Reprod. 55 (1996), 254) and human embryonic germ (hEG) cells (Shamblott et al., Proc. Natl. Acad. Sci. USA 95 (1998), 13726). Other types of pluripotent cells are also included in the term. Any cells of mammalian origin that are capable of producing progeny that are derivatives of all three germinal layers are included, regardless of whether they were derived from embryonic tissue, fetal tissue or other sources. The stem cells employed in accordance with the present invention are preferably (but not always necessarily) karyotypically normal. However, it is preferred not to use ES cells that are derived from a malignant source.

"Feeder cells" or "feeders" are terms used to describe cells of one type that are co-cultured with cells of another type, to provide an environment in which the cells of the second type can grow. The feeder cells are optionally from a different species as the cells they are supporting. For example, certain types of ES cells can be supported by primary mouse embryonic fibroblasts, immortalized mouse embryonic fibroblasts (such as murine STO cells, e.g., Martin and Evans, Proc. Natl. Acad. Sci. USA 72 (1975), 1441-1445), or human fibroblast-like cells differentiated from human ES cells, as described later in this disclosure. The term "STO cell" refers to embryonic fibroblast mouse cells such as are commercially available and include those deposited as ATCC CRL 1503.

The term "embryoid bodies" (EBs) is a term of art synonymous with "aggregate bodies". The terms refer to aggregates of differentiated and undifferentiated cells that appear when ES cells overgrow in monolayer cultures, or are maintained in suspension cultures. Embryoid bodies are a mixture of different cell types, typically from several germ layers, distinguishable by morphological criteria; see also infra. As used herein, "embryoid body", "EB" or "EB cells" typically refers to a morphological structure comprised of a population of cells, the majority of which are derived from embryonic stem (ES) cells that have undergone differentiation. Under culture conditions suitable for EB formation (e.g., the removal of Leukemia inhibitory factor or other, similar blocking factors), ES cells proliferate and form small masses of cells that begin to differentiate. In the first phase of differentiation, usually corresponding to about days 1-4 of differentiation for humans, the small mass of cells forms a layer of endodermal cells on the outer layer, and is considered a "simple embryoid body". In the second phase, usually corresponding to about days 3-20 post differentiation for humans, "complex embryoid bodies" are formed, which are characterized by extensive differentiation of ectodermal and mesodermal cells and derivative tissue. As used herein, the term "embryoid body" or "EB" encompasses both simple and complex embryoid bodies unless otherwise required by context. The determination of when embryoid bodies have formed in a culture of ES cells is routinely made by persons of skill in the art by, for example, visual inspection of the morphology. Floating masses of about 20 cells or more are considered to be embryoid bodies; see, e.g., Schmitt et al., Genes Dev. 5 (1991), 728-740; Doetschman et al. J. Embryol. Exp. Morph. 87 (1985), 27-45. It is also understood that the term "embryoid body", "EB", or "EB cells" as used herein encompasses a population of cells, the majority of which being pluripotent cells capable of developing into different cellular lineages when cultured under appropriate conditions. As used herein, the term also refers to equivalent structures derived from primordial germ cells, which are primitive cells extracted from embryonic gonadal regions; see, e.g., Shamblott, et al. (1998), supra. Primordial germ cells, sometimes also referred to in the art as EG cells or embryonic germ cells, when treated with appropriate factors form pluripotent ES cells from which embryoid bodies can be derived; see, e.g., U.S. Pat. No. 5,670,372; Shamblott, et al., supra.

If not stated otherwise the terms "compound", "substance" and "(chemical) composition" are used interchangeably herein and include, but are not limited to therapeutic agents (or potential therapeutic agents), agents of known toxicities such as neurotoxins, hepatic toxins, toxins of hematopoietic cells, myotoxins, carcinogens, teratogens, or toxins to one or more reproductive organs. The chemical compositions can further be agricultural chemicals, such as pesticides, fungicides, nematicides, and fertilizers, cosmetics, including so-called "cosmeceuticals", industrial wastes or by-products, or environmental contaminants. They can also be animal therapeutics or potential animal therapeutics.

Test substances that can be tested with the methods of the present invention comprise all kinds of chemicals, for example textile chemicals, laboratory chemicals, industrial chemicals, medical chemicals, printing chemicals, leather chemicals, in particular household products including bleaches, toilet, blocks, washing-up liquids, soap powders and liquids, fabric conditioners, window, oven, floor, bathroom, kitchen and carpet cleaners, dishwater detergents and rinse aids, water-softening agents, descalers, stain removers, polishes, paints, paint removers, lubricant, dyestuff, coating, glues, solvents, varnishes, air fresheners, moth balls insecticides and the like.

New ingredients for household products are constantly being developed and needed to be tested. For example, in recent years new enzymes (to digest stains) and "optical brighteners" (which make washing appear whiter) have been developed for use in washing powders and liquids. New surfactants (which cut through grease to remove ingrained dirt) and chemical "builders" (which act as water softeners and enable surfactants to work more effectively) have been developed for use in washing powders and liquids, washing-up liquids and various cleaning agents. But also medical materials have to be tested, for example dental materials such as new filling polymers, metal alloys, and bioactive ceramic. Furthermore, chemical compositions of any part of a device, such as an electrode, adhesives, paste, gel or cream including the concentrations of the different ingredients and impurities present may be tested with the method of the present invention.

DETAILED DESCRIPTION

Stem cells of various kinds have become an extremely attractive modality in regenerative medicine. They can be proliferated in culture, and then differentiated in vitro or in situ into the cell types needed. This plasticity makes them ideal models for toxicity testing. Particularly, embryoid bodies (EBs) which consist of different cell types of the three germ layers that interact with each other provide a highly sensitive test system. In one embodiment, the cells within an embryoid body are substantially synchronized for their differentiation. Accordingly, at known intervals, the majority of the synchronized cells differentiate into the three embryonic germ layers and further differentiate into multiple tissue types, such as cartilage, bone, smooth and striated muscle, and neural tissue, including embryonic ganglia. Thus, the cells within embryoid bodies provide a much closer model to the complexity of whole organisms than do traditional single cell or yeast assays, while still avoiding the costs and difficulties associated with the use of mice and larger mammals. Moreover, the recent availability of human embryoid bodies improves the predictive abilities of the invention by providing an even closer vehicle for modeling toxicity in human organ systems, and in humans. Thus, the provision of EBs in sufficient quantity and in an economically efficient manner is the main object of this invention.

Accordingly, the present invention relates to a method for producing embryoid bodies (EBs) from multi- or pluripotent cells comprising
(a) agitation of a liquid suspension culture of multi- or pluripotent cells in a container until generation of cell aggregates; and
(b) optionally diluting the suspension; and further agitation of the suspension until formation of EBs.

The present invention is based on agitation technique rather than EBs stirring or hanging drop cultures previously described as the method of choice.

In accordance with the present invention, it has surprisingly been found that embryonic stem (ES) cell aggregates, so called embryoid bodies (EBs) can be generated in large amounts and high density, which in turn can be induced to differentiate into particular cell types and tissue such as cardiomycytes, neurones, endothelial cells and the like. The present invention is based on the observation that agitation of a certain amount and concentration of ES cells in an appropriate container is superior to, for example, the stirring culture method for the preparation of ES cell aggregates, in particular embryoid bodies. Thus, in contrast to methods described in the prior art a culture system could be established that allows the generation of EBs in high density, which has no negative influence on the differentiation capacity towards different cell types such as cardiomyocytes, neurons, endothelial cells and liver cells. Moreover, compared with other methods, the method of the present invention does neither need sophisticated equipment like, e.g., fermenters of stirred bioreactors, nor time-consuming and laborious cell preparations like the encapsulation method described in international application WO03/004626. Thus, the advantage of the present invention is to generate large amounts of high-quality EBs with a simple and cheap method, which makes the method suitable for large-scale testing procedures like high throughput screening in drug discovery.

With the method of the invention the yield of embryoid bodies can be considerably be improved compared to conventional methods, since the cell aggregates can be cultured in large volumes and higher density than in the previous methods. The method of the invention also allows generating tissue in sufficient amounts for therapeutic uses, wherein the target tissue can be purified according to standard methods such as described in WO02/051987. Accordingly, the method of the present invention provides several advantages over the prior art methods for the preparation of embryoid bodies.

First, the embryoid bodies, and thus any desired precursors and cell types are provided in large amounts and high density and allow compound screening on industrial scale.

Second, the method of the invention is quite easy to perform contrary to, for example, the hanging drop method. In accordance with this, the method of the invention is much more reliable and reproducible than the classical methods.

Third, the operating expense for large-scale production of embryoid bodies in accordance with the method of the present invention is also quite low compared to other fermenter cultures.

Fourth, compared to cultures in spinner flasks, in the method of the invention the ES cells are much less exposed to shear stress, whereby the capability of the cells to differentiate in an appropriate manner is not negatively influenced.

Fifth, the preparation of large amounts of ES cell aggregates and tissue derived therefrom, respectively, under identical conditions ("batch") is important, e.g., for toxicological and pharmacological investigations and for the generation of tissue for transplantation purposes.

As described in the examples and figures, the method of the present invention can be generally described as follows:
1. Optionally conventional culturing of ES cells on feeder cells, for example, mouse embryonic fibroblasts;
2. Regarding the desired test or differentiation procedure, two different protocols (high density and low density cell suspension) are possible, as described in FIG. 1:
3. EB generation from high-density cell suspension (protocol 1): preparation of a cell suspension with a density of about 1 to $5 \times 10^6$ ES cells/ml, preferably 1.5 to $2.5 \times 10^6$ ES cells/ml, most preferably about $2 \times 10^6$ ES cells/ml and transfer in an appropriate container such as petri dish;
4. Agitating the suspension for about six hours on a rocking table at about 50 rpm until generation of cell aggregates;
5. Dilution of the suspension 1:10 or 1:20 and transfer into an appropriate second container such as preferably T25 flasks;
6. Further agitating the suspension for about 12 to 18, preferably to a total (steps (a) and (b)) of 16 to 20, most preferably 18 hours on the rocking table; optionally
7. Dividing cell aggregates to the final and desired concentration; adding of test compounds (optionally).
8. EB generation from low-density cell suspension (protocol 2): preparation of a cell suspension with a density of about $0.1-0.5 \times 10^6$ ES cells/ml, most preferably $0.2 \times 10^6$ cells/ml and transfer in an appropriate container such as a petri dish;
9. Agitating the suspension for about 48 hours on a rocking table at about 50 rpm until generation of cell aggregates;
10. Dilution of the suspension to the final and desired concentration of EBs, preferably 100-2000 EBs/10 ml in an appropriate container such as a petri dish;
11. Differentiating the cells either in suspension or after plating on appropriate surfaces, such as collagen-coated cell culture dishes, into the desired tissue; optionally
12. Selection of desired differentiated cell types and tissue with the help of preferably resistance markers, for example puromycin selection; and optionally
13. Use of the embryoid bodies, cells or tissue for a variety of in vitro tests such as cardiotoxicity assay as described in the examples, or for therapeutic uses such as transplantation.

Both protocols described above resulted in equal amounts of EBs per initial petri dish. The low density method has the advantage to generate approx. 10 times more EBs from the same amount of ES cells, but EBs can not be processed during the first 48 hours. The high density protocol has the advantage of generating stable EBs already after 12 to 18 hours, which is crucial for several test procedures such as embryotoxicity testing or manipulation of stem cell fate during early germ layer formation.

Figure 1:
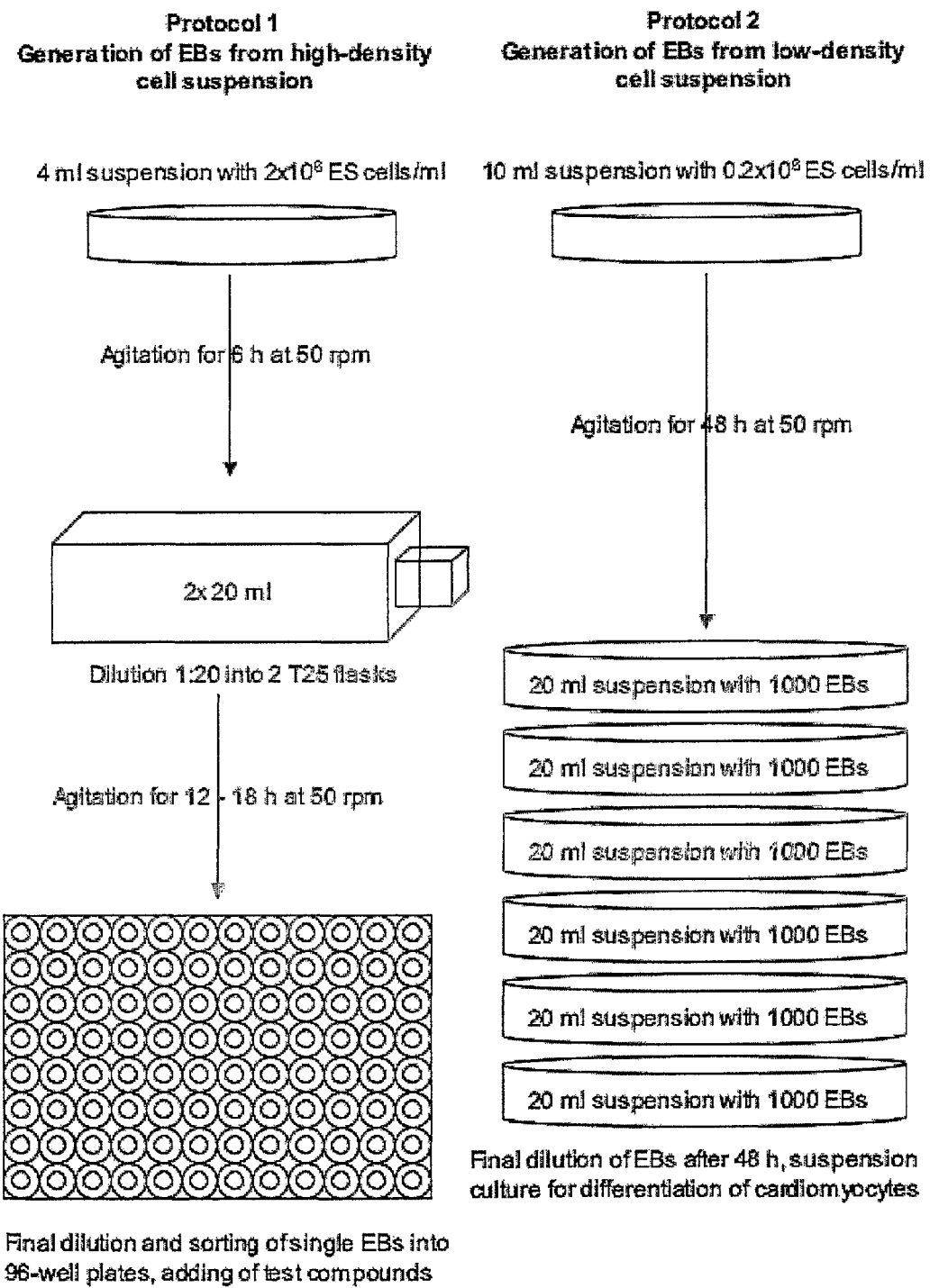
FIG. 1: Row chart of 2 different protocols to generate EBs by agitation culture.
Figure 2:
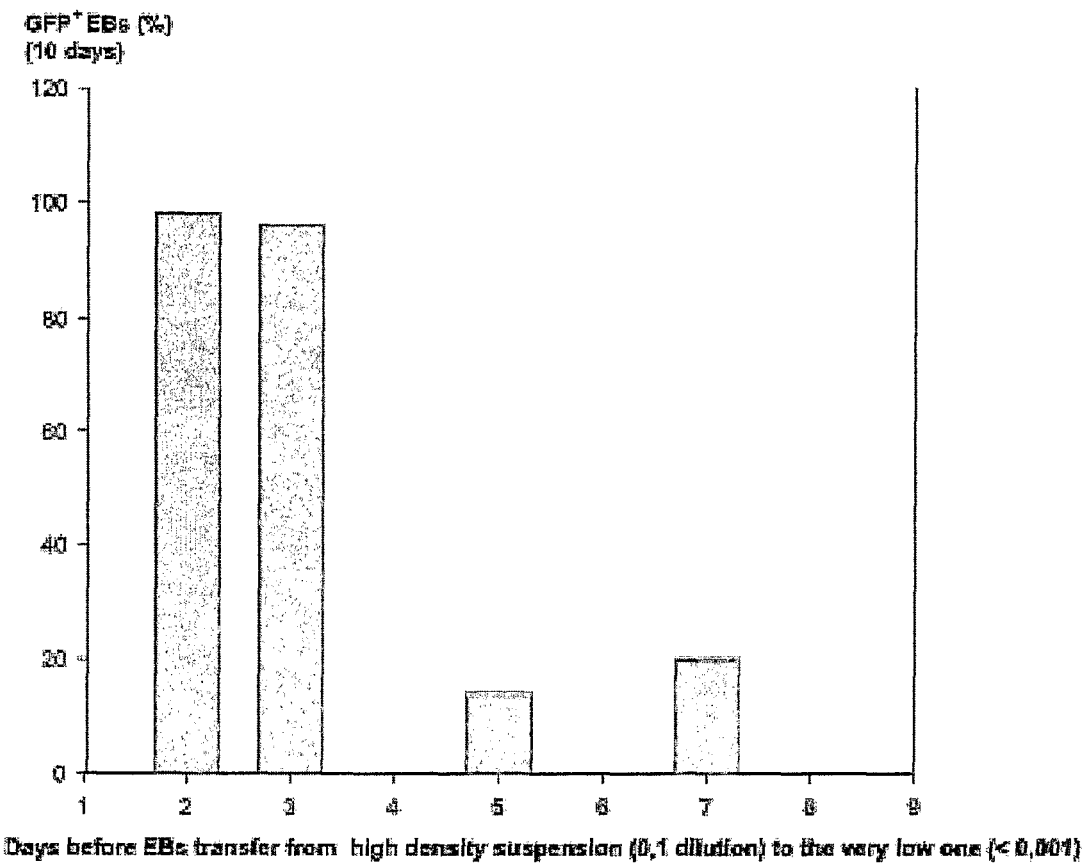
FIG. 2: Cardiac differentiation of the ES cells (clone αMHC-23) as a function of the day of withdrawal of EBs from the high density suspension. Effect of time point of final dilution of EB suspension on cardiac differentiation. Y axis (GFP*EBs (%)) represents relative amount of cardiac cells within EBs.

Thus, as evident from the above and illustrated in FIG. 1, the dilution step in step (b) of the method of the invention is optionally and depending on the initial concentration of ES cells. Thus, when an initial cell density of about 1 to $5 \times 10^6$ ES cells/ml is used, protocol 1 is preferably used while protocol 2 may be advantageous for a cell density below $10^6$ ES cells/ml. Of course, as will be acknowledged by the person skilled in the art, the decision whether to use protocol 1 or 2 with an initial cell density of 0.5 to $1 \times 10^6$ ES cells/ml may be decided on a case by case basis and most probably will depend on the intended use of the embryoid bodies. Thus, for the purposes of single EBs screening, preferably high density cell suspensions with protocol 1 are used, while for other purposes such as the provision of tissue grafts or investigation of tissue structure formation and the like the use of low density cell suspensions with protocol 2 may be more appropriate.

The invention can be practiced using stem cells of any vertebrate species. Included are stem cells from humans as well as non-human primates, domestic animals, livestock, and other non-human mammals. Amongst the stem cells suitable for use in this invention are primate pluripotent stem cells derived from tissue formed after gestation, such as a blastocyst, or fetal or embryonic tissue taken any time during gestation. Non-limiting examples are primary cultures or established lines of embryonic stem cells. The invention is also applicable to adult stem cells. It is referred to the literature of Anderson et al., Nat. Med. 7 (2001), 393 395, and Anderson et al., 2001, Gage, F. H., 200, and Prockop, Science 276 (1997), 71-74, wherein the extraction and culture of those cells is described. Thus, said multi- or pluripotent cells used in accordance with the method of the present invention are usually embryonic stem (ES) cells, primordial germ (EG) cells or adult stem cells, most preferably ES cells.

As mentioned before, several sources for ES cells are at the disposal of the skilled person of which human stem cells are preferred for most of the embodiments of the present invention, in particular for therapeutic purposes such as transplantation. Human embryonic stem cells and their use for preparing different cell and tissue types are also described in Reprod. Biomed. Online 4 (2002), 58-63. Embryonic stem cells can be isolated from blastocysts of members of the primate species (Thomson et al., Proc. Natl. Acad. Sci. USA 92 (1995), 7844). Human embryonic germ (EG) cells can be prepared from primordial germ cells present in human fetal material taken about 8-11 weeks after the last menstrual period. Suitable preparation methods are described in Shamblott et al., Proc. Natl. Acad. Sci. USA 95 (1998), 13726. Methods for making cells that resemble embryonic stem cells or embryonic germ cells in morphology and pluripotency derived from primordial germ cells isolated from human embryonic tissue, such as from the gonadal ridges of human embryo, are described in U.S. Pat. No. 6,245,566.

Recently, is has been reported that exfoliated human deciduous tooth, a comparable very accessible tissue, contains multipotent stem cells that were identified to be a population of highly proliferative, clonogenic cells capable of differentiating into a variety of cell types including neural cells, adipocytes, and odontoblasts; see Miura et al., Proc. Natl. Acad. Sci. USA 100 (2003), 5807-5812. After in vivo transplantation, those cells were found to be able to induce bone formation, generate dentin, and survive in mouse brain along with the expression of neural markers. Furthermore, multilineage potential of homozygous stem cells derived from metaphase II oocytes has been described by Lin et al. in Stem Cells 21 (2003), 152-161. Various sources of precursor cells in postnatal muscles and the factors that may enhance stem cell participation in the formation of new skeletal and cardiac muscle in vivo are reviewed in Grounds et al. J. Histochem. Cytochem. 50 (2002), 589-610. Purification of rare hematopoietic stem cell(s) (HSC) to homogeneity that home to bone marrow is described in US2003/0032185. These adult bone marrow cells are described to have tremendous differentiative capacity as they can also differentiate into epithelial cells of the liver, lung, GI tract, and skin. This finding may contribute to clinical treatment of genetic disease or tissue repair. Furthermore, techniques such as nuclear transfer for embryo reconstruction may be employed, wherein diploid donor nuclei are transplanted into enucleated MII oocytes. This technology along with other procedures that aid in the establishment of customized embryonic stem (ES) cell lines that are genetically identical to those of the recipient have been reviewed by Colman and Kind, Trends Biotechnol. 18 (2000), 192-196. In order to avoid graft rejection associated with allogenic or xenogenic cells in transplantation syngenic or autologous cells and recipients are preferably used in the corresponding embodiments of the invention. In view of the recently discovered sources of stem cells such as from the bone marrow and tooth it should be possible to accomplish this demand without the need to resort to embryonic cells and tissue. Alternatively, cells may be genetically manipulated to suppress relevant transplantation antigens, see also infra, immunosuppressive agents may be used. The field of stem cell technology is being reviewed by Kiessling and Anderson, Harvard Medical School, in Human Embryonic Stem Cells: An Introduction to the Science and Therapeutic Potential; (2003) Jones and Bartlett Publishers; ISBN: 076372341X.

In order to avoid the use of, for example, human embryos as the donor for stem cells, which however seems to be justifiable at least under certain circumstances, it may even be possible to employ transgenic non-human animals, in particular mammals as source for embryonic stem cells. For example, compositions and methods for making transgenic swines to be used as xenograft donors is described in U.S. Pat. No. 5,523,226. Likewise, WO97/12035 describes methods of producing transgenic animals for xenotransplantation. Furthermore, immunologically compatible animal tissue, suitable for xenotransplantation into human patients, is described in WO01/88096. Methods for making embryonic germ cells from porcine are described for example in U.S. Pat. No. 6,545,199.

In a particularly preferred embodiment, especially for screening purposes, the stem cell to be used in accordance with the present invention is derived from a murine ES cell line, for example, the R1 cell line (ATCC No. SCRC-1011) described by Nagy et al., Proc. Natl. Acad. Sci. USA 90 (1993), 8424-8428, and cell line D3; see also Example 1.

Stem cells can be propagated continuously in culture, using a combination of culture conditions that promote proliferation without promoting differentiation. Traditionally, stem cells are cultured on a layer of feeder cells, typically fibroblast-type cells, often derived from—embryonic or fetal tissue. The cell lines are plated to near confluence, usually irradiated to prevent proliferation, and then used to support when cultured in a medium conditioned by certain cells (e.g. Koopman and Cotton, Exp. Cell 154 (1984), 233-242; Smith and Hooper, Devel. Biol. 121 (1987), 1-91), or by the exogenous addition of leukemia inhibitory factor (LIF). Such cells can be grown relatively indefinitely using the appropriate culture conditions. In a preferred embodiment of the method of the invention, the cells are cultured on embryonic mouse fibroblasts prior to step (a); see also supra.

In principle, any conventional culture medium can be used in the methods of the present invention such as media for isolating and propagating stem cells that can have any of several different formulas, as long as the cells obtained have the desired characteristics, and can be propagated further. Suitable sources include Iscove's modified Dulbecco's medium (IMDM), Gibco, #12440-053; Dulbecco's modified Eagles medium (DMEM), Gibco #11965-092; Knockout Dulbecco's modified Eagles medium (KO DMEM), Gibco #10829-018; 200 mM L-glutamine, Gibco #15039-027; non-essential amino acid solution, Gibco 11140-050; [beta]-mercaptoethanol, Sigma # M7522; human recombinant basic fibroblast growth factor (bFGF), Gibco #13256-029. Exemplary serum-containing ES medium and conditions for culturing stem cells are known, and can be optimized appropriately according to the cell type. Media and culture techniques for particular cell types referred to in the previous section are provided in the references cited herein.

However, preferred is the use of IMDM with 20% FCS at $CO_2$ of 5% while DMEM with 20% FCS at 7% $CO_2$ can also be used but is less preferred. Thus, in a particularly preferred embodiment of the method of the present invention, the culture medium in step (a) and/or in step (b) is IMDM 20% FCS and 5% $CO_2$.

Other culture conditions can be adjusted according to standard methods known to the person skilled in the art. Particularly preferred, however, is to perform the method of the present invention, wherein the culture conditions in step (a) and/or (b), most preferably in both steps and during the complete culture period, comprise 37° C. and 95% humidity.

In a particularly preferred embodiment, the method of the invention according to protocol 1 is performed, wherein the suspension in step (a) is cultured for about 6 hours and/or in step (b) for a total of about 18 hours. While the time for the first culturing step may be more critical and therefore the indicated time of about six hours should be kept as close as possible, the total culturing time including the second culturing step, i.e. step (b) may vary for example from about 16 to 20 hours. After this time, ES cell aggregates ("embryoid bodies", EBs) of homogeneous shape and size are formed, typically around 500 per ml of suspension. The first protocol is particularly advantageous when toxicological tests are subsequently performed, since the cell aggregates are fresh and most viable after a culturing time in step (b) of about 12 to 18 hours. Regarding the desired test or differentiation procedure, two different protocols (high density and low density cell suspension) are possible, as described in FIG. 1. As mentioned above, in this embodiment the density of the starting cell suspension is preferably about 1 to $5 \times 10^6$ ES cells/ml, most preferably about $2 \times 10^6$ ES cells/ml.

However, in an alternative embodiment of the method of the present invention i.e. according to protocol 2 it is also possible to use a lower cell density of about $10^5$ to $10^6$, preferably about 1 to $5 \times 10^5$ ES cells/ml, and most preferably about $2\times10^5$ ES cells/ml for certain purposes, e.g., for generation of tissue or tissue-like structures useful for, e.g., transplantation or investigation of tissue formation. In this embodiment steps (a) and (b) are combined, i.e. there is no dilution step but a continuous step of culturing and agitating the cell suspension until formation of EBs, wherein, the culturing time of the method of the invention is extended, usually to a total of about 36 to 60 hours, preferably to about 48 hours (±1, 2, 3, 4, or 5 hours or even 1-10 hours, which may be experimentally determined if necessary).

Of course, the person skilled in the art may vary one or more parameters indicated herein for the method of the present invention while still working along the gist of the invention that is the use of a liquid suspension culture of multi- or pluripotent cells being constantly agitated, preferably horizontally during a defined period of time, optionally including a transfer of the cell suspension until cell aggregates have been generated.

The container to be used in step (a) and (b) can be of any conventional type used in cell culture systems and can be of any appropriate material such as glass or preferably plastic. With respect to culturing cell suspension in step (a) round containers such as petri dishes are preferred. Without intending to be bound by theory it has been observed in experiments performed in accordance with the present invention that the shape of the container may have some influence on the yield and the status of the cells and cell aggregates, respectively. It has thus been found that for the first culture step of the liquid suspension culture of multi- or pluripotent cells round containers such as petri dishes are preferably used. In this respect, for the high density protocol a ratio of for example 4 ml of cell suspension to 6 cm (diameter) petri dish was found to give very good results. For the low density protocol, a ratio of 10 ml of cell suspension to 10 cm (diameter) petri dish was found to give the best results. Therefore, the container in step (a), and optionally step (b) should be preferably chosen such that a corresponding ratio of cell suspension and culture surface of the container as described in the examples is achieved.

Similarly, in step (b) of the high density protocol the container, for example, culture flask, should preferably be dimensioned as described in the examples for the T25 flasks. Furthermore, in accordance with the dimension of the containers used in the method of the present invention, the rate of agitation should be adjusted accordingly. Typically, the agitation in step (a) and/or (b) is performed at 50 rpm. However, different rates for containers deviating from those used in the examples may be used as well.

Thus, in a further preferred embodiment of the present invention, the incubation step is conducted in a container made of plastic, and wherein the suspension culture in step (a) is present in a petri dish and/or in step (b) in a culture flask, beaker or tumbler, most preferably in T25 flasks, preferably with agitation at 50 rpm. The agitation in step (a) and/or (b) is preferably a horizontal agitation. However, other agitation procedures such as tumbling may be used as well while however less preferred.

In the high density protocol, after step (a) the cell suspension, i.e. cell aggregates are diluted by a factor of about 5 to 20, preferably by a factor of about 10. The actual factor may vary due to, for example, the initial concentration of multi- or pluripotent cells. Generally, the dilution in step (b) is preferably at least about $\geq 1:5$, more preferably about 1:10 or higher, for example 2 ml of the suspension obtained in step (a) with 18 ml new medium such as IMDM 20% FCS; see also the examples. Most preferably, the dilution factor is 1:10 in case the initial concentration of multi- or pluripotent cells compares to $2\times10^6$ cells/ml.

Figure 3:
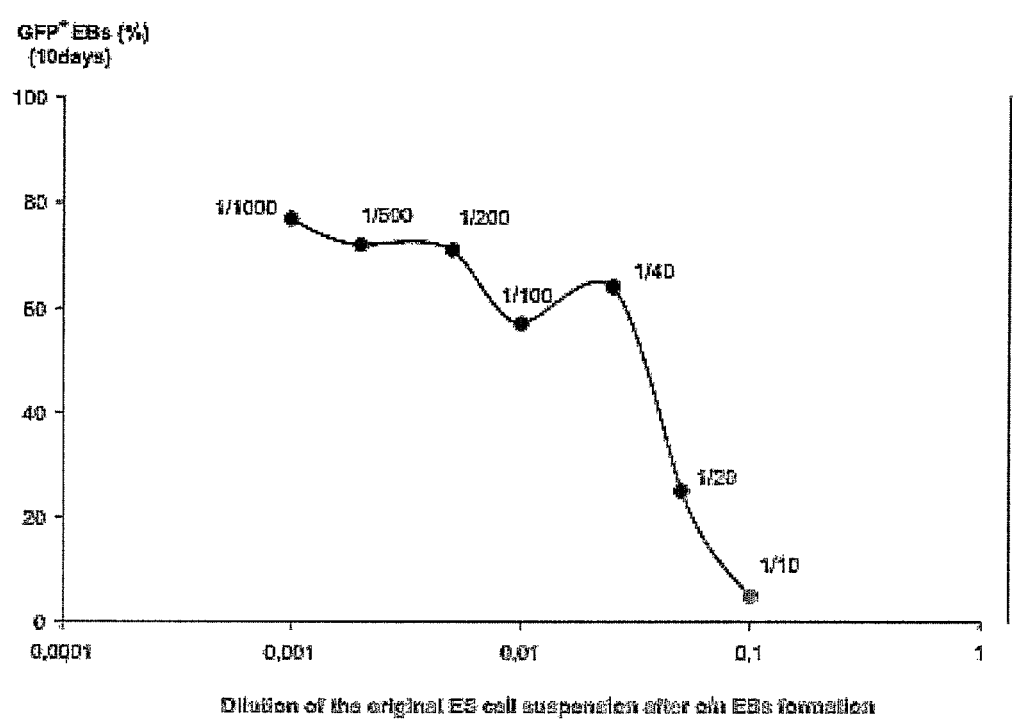
FIG. 3: Cardiac differentiation of the ES cells (clone αMHC-23) as function of the EBs density. Effect of final dilution factor of EB suspension on cardiac differentiation. Y axis (GFP*EBs (%)) represents relative amount of cardiac cells within EBs.

For the low density protocol, the final dilution step of EBs is performed directly from the initial suspension. Most preferably, the dilution should result in an EB density of 100-2000 EBs per 10 ml of medium, regarding the desired test or differentiation protocol and the containers that should be used for further culture. A higher EB density may result in loss of differentiation capacity, as indicated in FIG. 3 for cardiac differentiation.

In previous methods for the production of embryoid bodies the yield of embryoid bodies was in a range of 50/ml. With the method of the present invention, however, final concentrations of EBs in a suspension culture of step (b) are possible in a range of 100 to of about more than 1.000/ml, generally in a range of about 500/ml. Preferably, the method according to protocol 1 is performed such that the culture reaches a concentration of about >500/ml EBs. Thus, even with an experimental set up for the production of embryoid bodies in accordance with the present invention, about 10.000 embryoid bodies can be generated in one experiment (starting with ES cells from one 6 cm petri dish), which allows the performance of various tests concomitantly and in parallel. This is particularly advantageous for compound screening, since several dilutions of the test compounds have to be tested and various standard compounds in order to compare them as a profile with those of the test compounds are usually employed in such screening methods. Thus, the method of the present invention for the first time enables the use of embryoid bodies for compound screening in a cost-effective manner and on a reasonable industrial scale.

After completion of the essential steps of the method of the present invention, further steps can be performed such as dividing the cell aggregates obtained in step (b) to the desired final concentration, for example for use in toxicity tests and/or for the production of certain cell types and tissue.

In the absence of feeder cells, exogenous leukemia inhibitory factor (LIF), or conditioned medium, ES or EG cells in the form of embryoid bodies spontaneously differentiate into a wide variety of cell types, including cells found in each of the endoderm, mesoderm and ectoderm germ layers. With the appropriate combinations of growth and differentiation factors, however, cell differentiation can be controlled. For example, EB cells can generate cells of the hematopoietic lineage in vitro (Keller et al., Mol. Cell Biol. 13 (1993), 473-486; Palacios et al., Proc. Natl. Acad. Sci. USA 92 (1995), 7530-7534; Rich, Blood 86 (1995), 463-472). Additionally, mouse ES cells have been used to generate in vitro cultures of neurons (Bain et al., Developmental Biology 168 (1995), 342-357; Fraichard et al., J. Cell Science 108 (1995), 3161-3188), cardiomyocytes (heart muscle cells) (Klug et al., Am. J. Physiol. 269 (1995), H1913-H1921), skeletal muscle cells (Rohwedel et al., Dev. Biol. 164 (1994), 87-101), vascular cells (Wang et al., Development 114 (1992), 303-316). U.S. Pat. No. 5,773,255 relates to glucose-responsive insulin-secreting pancreatic beta cell lines, U.S. Pat. No. 5,789,246 relates to hepatocyte precursor cells. Hepatic differentiation of murine embryonic stem cells is also described in Jones et al., Exp. Cell Res. 272 (2002), 15-22.

Other progenitors of interest include, but are not limited to chondrocytes, osteoblasts, retinal pigment epithelial cells, fibroblasts, epithelial cells, skin cells such as keratinocytes, dendritic cells, hair follicle cells, renal duct epithelial cells, smooth and skeletal muscle cells, liver cells, testicular progenitors, and vascular endothelial cells. Embryonic stem cell differentiation models for cardiogenesis, myogenesis, neurogenesis, epithelial and vascular smooth muscle cell differentiation in vitro have been generally described in Guan et al., Cytotechnology 30 (1999), 211-226.

In certain embodiments of the invention, differentiation is promoted by withdrawing one or more medium component(s) that promote(s) growth of undifferentiated cells, or act(s) as an inhibitor of differentiation. Examples of such components include certain growth factors, mitogens, leukocyte inhibitory factor (LIF), and basic fibroblast growth factor (bFGF). Differentiation may also be promoted by adding a medium component that promotes differentiation towards the desired cell lineage, or inhibits the growth of cells with undesired characteristics.

Hence, in a further embodiment the method of the present invention further comprises culturing the cells and cell aggregates, i.e. embryoid bodies, respectively, under conditions allowing differentiation of the cells into at least one cell type such as those mentioned above.

Of course, the multi- or pluripotent cells used for the production of the embryod bodies in accordance with the method of the present invention may not be native but genetically engineered, for example with reporter gene constructs and/or other transgenes, for example such of which the function in cell development and differentiation is desired to be elucidated. Furthermore, as mentioned above, in accordance with this invention embryoid bodies obtained by the above described methods can be induced to develop particular cell types and tissue. Populations of differentiated cells can be depleted of relatively undifferentiated cells and/or of cells of undesired cell types by using a selection system that is lethal to the undesired cells and cell types, i.e. by expressing a selectable marker gene that renders cells of a specific cell type resistant to a lethal effect of an external agent, under control of a regulatory sequence that causes the gene to be preferentially expressed in the desired cell type and/or at a certain stage of development. To accomplish this, the cells are genetically altered before the process used to differentiate the cells into the desired lineage for therapy, in a way that the cells comprise a selectable marker operably linked to a cell type-specific regulatory sequence specific for the desired cell type.

Any suitable expression vector for this purpose can be used. Suitable viral vector systems for producing stem cells altered according to this invention can be prepared using commercially available virus components. The introduction of the vector construct or constructs into the embryonic stem cells occurs in a known manner, e.g. by transfection, electroporation, lipofection or with the help of viral vectors. Viral vectors comprising effector genes are generally described in the publications referenced in the last section. Alternatively, vector plasmids can be introduced into cells by electroporation, or using lipid/DNA complexes. Exemplary is the formulation Lipofectamine 2000™, available from Gibco/Life Technologies. Another exemplary reagent is FuGENE™ 6 Transfection Reagent, a blend of lipids in non-liposomal form and other compounds in 80% ethanol, obtainable from Roche Diagnostics Corporation. Preferably, the vector constructs and transfection methods described in WO02/051987 are used, the disclosure content of which is incorporated herein by reference.

Resistance genes per se are known. Examples for these are nucleoside and aminoglycoside-antibiotic-resistance genes conferring resistance to, e.g., puromycin, neomycin or hygromycin. Further examples for resistance genes are dehydrofolate-reductase, which confers a resistance against aminopterine and methotrexate, as well as multi drug resistance genes, which confer a resistance against a number of antibiotics, e.g. against vinblastin, doxorubicin and actinomycin D.

In a particularly preferred embodiment of the present invention, said selectable marker confers resistance to puromycin. Puromycin is particularly suited for the fast elimination of non-cardiac cells in adherent culture of transgenic EBs. Furthermore, drug selection of cardiac cells can be implemented entirely in the suspension culture of transgenic EBs. Hence, it could also be shown that purified ES cell-derived cardiomyocytes survive much longer in culture than untreated counterparts. Moreover, the elimination of undifferentiated ES cells during drug selection process has itself been shown to have clear positive effect on viability and longevity of such differentiated ES cell-derived cells as cardiomyocytes. In addition, it could be surprisingly shown that the release from surrounding non-differentiated cells induces proliferation of cardiomyocytes. Thus, the drug selection possesses both purifying and multiplying effect.

In a preferred embodiment of the invention, said multi- or pluripotent cells of said EBs comprise a reporter gene, preferably wherein said reporter is operably linked to a cell type-specific regulatory sequence specific for a certain cell type. This type of vector has the advantages of providing visualization of differentiation, definition of the time point for beginning of drug selection, visualization of drug selection and tracing of the fate of purified cells grafted in recipient tissue. Such vectors, which are preferably employed in accordance with the methods of the present invention are described in WO02/051987. Usually, said cell type-specific regulatory sequence of the reporter gene is substantially the same as said cell type-specific regulatory sequence of the marker gene. This can advantageously be achieved by putting said marker gene and said reporter gene into the same recombinant nucleic acid molecule, i.e. vector used for stem cell transfection, preferably such that said marker gene and said reporter gene are contained on the same cistron.

The reporter can be of any kind as long as it is non-damaging for the cell and confers an observable or measurable phenotype. According to the present invention, the green fluorescent protein (GFP) from the jellyfish Aequorea victoria (described in WO95/07463, WO96/27675 and WO95121 191) and its derivates "Blue GFP" (Heim et al., Curr. Biol. 6 (1996), 178-182 and Redshift GFP" (Muldoon et al., Biotechniques 22 (1997), 162-167) can be used. Particularly preferred is the enhanced green fluorescent protein (EGFP). Further embodiments are the enhanced yellow and cyan fluorescent proteins (EYFP and ECFP, respectively) and red fluorescent proteins (DsRed, HcRed). Further fluorescent proteins are known to the person skilled in the art and can be used according to the invention as long as they do not damage the cells. The detection of fluorescent proteins takes place through per se known fluorescence detection methods; see, e.g., Kolossov et al., J. Cell Biol. 143 (1998), 2045-2056. Alternatively to the fluorescent proteins, particularly in in vivo applications, other detectable proteins, particularly epitopes of those proteins, can also be used. Also the epitope of proteins, though able to damage the cell per se, but whose epitopes do not damage the cells, can be used; see also WO02/051987.

For the selection of stably transfected ES cells vector constructs contain a further selectable marker gene, which confers, e.g., a resistance against an antibiotic, e.g., neomycin. Of course, other known resistance genes can be used as well, e.g., the resistance genes described above in association with the fluorescent protein-encoding genes. The selection gene for the selection of stably transfected ES cells is under the control of a different promoter than that which regulates the control of the expression of the detectable protein. Often constitutively active promoters are used, e.g., the PGK-promoter.

The use of a second selection gene is advantageous for the ability to identify the successfully transfected clones (efficiency is relatively low) at all. Otherwise a smothering majority of non-transfected ES cells may exist and during differentiation, e.g., no EGFP-positive cells might be detected.

In a further embodiment of the invention, the cells can be manipulated additionally so that specific tissues are not formed. This can occur for instance by insertion of repressor elements, e.g., a doxicyclin-inducible repressor element. Thereby, a possible contamination of the desired differentiated cells with pluripotent, potentially tumorigenic cells can also be excluded.

The desired cell type intended for the stem cells and embryoid bodies to differentiate to may be of any kind and includes, but is not limited to neuronal cells, glial cells, cardiomyocytes, glucose-responsive insulin-secreting pancreatic beta cells, hepatocytes, astrocytes, oligodendrocytes, chondrocytes, osteoblasts, epithelial cells, retinal pigment epithelial cells, fibroblasts, keratinocytes, dendritic cells, hair follicle cells, renal duct epithelial cells, vascular endothelial cells, testicular progenitors, smooth and skeletal muscle cells; see also supra.

In a particularly preferred embodiment of the invention, said cell type are cardiomyocytes. For this embodiment, a cell type-specific regulatory sequence for driving a drug resistance gene is used, which is preferably atrial- and/or ventricular-specific. Corresponding regulatory sequences, i.e. cardiac-specific promoters are described for Nkx-2.5 specific for very early cardiomyocytes and mesodermal precursor cells respectively, (Lints et al., Development 119 (1993), 419-431); human-cardiac-α-actin specific for heart tissue, (Sartorelli et al., Genes Dev. 4 (1990), 1811-1822), and MLC-2V specific for ventricular heart muscle cells (O'Brien et al., Proc. Natl. Acad. Sci. U.S.A. 90 (1993), 5157-5161 and WO-A-96/16163). Cardiac-specific alpha-myosin heavy chain promoter is described in Palermo et al., Cell Mol. Biol. Res. 41 (1995), 501-519; Gulick et al., J. Biol. Chem. 266 (1991), 9180-91855; the myosin light chain-2v (MLC2v) promoter also by Lee et al., Mol. Cell Biol. 14 (1994), 1220-1229; Franz et al., Circ. Res. 73 (1993), 629-638; see also expression of the atrial-specific myosin heavy chain AMHC1 and the establishment of anteroposterior polarity in the developing chicken heart described in Yutzey et al., Development 120 (1994), 871-883.

Another cell type are fibroblasts which can also be generated de novo from ES cells in accordance with the method of the present invention. Thus, ES cells are transfected with a recombinant nucleic acid molecule comprising a marker and optionally a reporter gene operatively linked to a cell type-specific regulatory sequence, i.e. a fibroblast-specific promoter such as the a2 (I) collagen promoter though also active in bone cells; Lindahl et al., J. Biol. Chem. 277 (2002), 6153-6161; Zheng et al., Am. J. Pathol. 160 (2002), 1609-1617; Antoniv et al., J. Biol. Chem. 276 (2001), 21754-21764; see also Finer, et al., J. Biol. Chem. 262 (1987), 13323-13333; Bou-Gharios et al., J. Cell Biol. 134 (1996), 1333-1344; Zheng et al., Am. J. Pathol. 160 (2002), 1609-1617; Metsaranta et al., J. Biol. Chem. 266 (1991) 16862-16869.

A further cell type are endothelial cells which can be derived from ES cells transfected with a vector construct as generally described before, wherein said cell type-specific regulatory sequence is an endothelial-specific promoter; see, e.g., vascular endothelial-cadherin promoter described by Gory et al., Blood 93 (1999), 184-192; the Tie-2 promoter/enhancer by Schlaeger et al., Proc. Natl. Acad. Sci. USA 94 (1997), 3058-3063; the Flk-1 promoter/enhancer by Kappel et al., Biochem. Biophys. Res. Commun. 276 (2000), 1089-1099.

Further cell- and tissue-type specific promoters are known; see, e.g., chondrocyte-specific pro-alphaI (II) collagen chain (collagen 2) promoter fragment described by Zhou et al., J. Cell Sci. 108 (1995), 3677-3684; neural alpha-1 tubulin-specific promoter described in Gloster et al., J. Neurosci. 14 (1994); 7319-7330 and glial fibrillary acidic protein (GFAP) promoter in Besnard et al., J. Biol. Chem. 266 (1991), 18877-18883. Further examples for tissue-specific promoters are those which are active in glia cells, hematopoietic cells, neuronal cells, preferably embryonal neuronal cells, endothelial cells, cartilage cells or epidermal cells as well as insulin-secreting β-cells. "Tissue specific" is to be subsumed under the term "cell-specific".

Further examples for non-heart-specific promoters are: PECAM1, FLK-1 (endothelium), nestine (neuronal precursor cells), tyrosin-hydroxylase-1-promoter (dopaminergic neurons), smooth muscle α-actin, smooth muscle myosin (smooth muscles), α1-fetoprotein (endoderm), smooth muscle heavy chain (SMHC minimal promoter (specific for smooth muscles, (Kallmeier et al., J. Biol. Chem. 270(1995), 30949-30957).

The term development-specific promoter refers to promoters that are active during certain points of time during development. Examples for such promoters are the β-MHC promoter that is expressed during embryonal development in the ventriculum of the mouse and is superseded by the α-MHC promoter in the prenatal phase; NKx2.5, a promoter during the early mesoderm/heart development; atrial-natriuretic-factor, a marker of the early embryonal heart with exception of the pacemaker, that is down-regulated also in later developmental stages; Flk-1, an endothelium-specific promoter that is active during the early vasculogenesis; intron 2-segment of the nestine gene that is expressed in neuronal precursor cells (embryonal neurons and glia cells) and adult glia cells (partially still able to divide) (Lothian and Lendahl, Eur. J. Neurosci. 9 (1997), 452-462U).

For the embodiments described hereinbefore, said resistance gene and said reporter gene are preferably contained in a bicistronic vector and are preferably separated by an IRES. Particularly preferred is the use of a construct, wherein said resistance gene confers resistance to puromycin, said marker is EGFP and said promoter is the cardiac αMHC promoter; see also the examples. In the above described embodiments concerning the generation of EBs essentially consisting of cardiac cells the EBs obtainable by the present invention usually and advantageously comprise functional cardiac tissue that beats autonomously and covers electrophysiological properties of atrial and ventricular cardiomyocytes as well as of pacemaker cells.

The present invention also relates to embryoid bodies and differentiated cells and tissue derived from said embryoid bodies. Hence, said cells are preferably embryonic cell type- and/or tissue-specific cells, most preferably cardiac tissue. Likewise, organs constituted from those cells, cell aggregates and tissue are subject of the present invention as well as implants or transplants comprising such cells, cell aggregates, tissue or organs. All of those can be used in a method of treatment of damaged tissue or organs in a subject comprising implanting or transplanting to the subject in need thereof. Hence, compositions such as pharmaceutical compositions comprising any one of those cell aggregates or tissue of the present invention as described herein are encompassed in the scope of the present invention. As described before, those compositions and methods of the invention can be used for a variety of purposes, for example for analyzing early steps of tissue formation during embryonic development or the influence of factors and compounds on this process. Furthermore, the EBs can be used for the preparation of transgenic non-human animals. The generation of transgenic animals from ES cells is known in the art; see, e.g., A. L. Joyner Ed., Gene Targeting, A Practical Approach (1993), Oxford University Press. A general method for making transgenic non-human animals is described in the art, see for example WO94/24274.

Hence, the present invention generally relates to the use of the afore-described method of the present invention, the embryoid bodies obtained thereby as well as differentiated cells and tissue thereof for loss of function assays of specific genes, gain of function assays of exogenous genes, developmental analysis of teratogenic/embryotoxic compounds, organ-specific analysis of toxic compounds, e.g., cardiotoxic or neurotoxic compounds, pharmacological assays, microarray systems, establishment of model systems for pathological cell functions, application of differentiation and growth factors for induction of selectively differentiated cells or as a source for tissue grafts. In one embodiment, the fate of the cell types and formation of cell aggregates and tissue as well as the physiological and/or developmental status of the cells or cell aggregate are analyzed, for example by isometric tension measurements, echocardiography and the like. Preferably, the status of the cells or cell aggregates is analyzed by monitoring the differentiation of electrical activity of the cells on an array, for example by recording the extracellular field potentials with a microelectrode array (MEA). For example, electrophysiological properties during the ongoing differentiation process of embryonic stem cells differentiating into cardiac myocytes can be followed by recordings of extracellular field potentials with microelectrode arrays (MEA) consisting of, e.g., 60 substrate-integrated electrodes; see Banach et al. Am. J. Physiol. Heart Circ. Physiol. (2003), February 6, p S0363-6135. Multiple arrays of tungsten microelectrodes were used to record the concurrent responses of brain stem neurons that contribute to respiratory motor pattern generation; see Morris et al., Respir. Physiol. 121 (2000), 119-133.

The EBs and methods of the present invention are particularly suited for use in drug screening and therapeutic applications. For example, differentiated EBs of this invention can be used to screen for substances (such as solvents, small molecule drugs, peptides, polynucleotides, and the like), particularly household products, see supra, or environmental conditions (such as culture conditions or manipulation) that affect the characteristics of differentiated cells. General as well as specific characteristics of differentiated cells, in particular embryoid bodies, are known to the person skilled in the art. Furthermore, test kits for the detection of cell-specific characteristics, i.e. markers and for determining the effect of a given test compound on the EB, for example by performing vitality tests such as MTT, XTT, LDH, etc., as well as methods for determining apoptosis, for example by measuring the amount or activity of caspase, annexin, etc., are well-known to the person skilled in the art. For review see, for example, the NIH publication No. 01-4499 on the report of the International Workshop on In Vitro Methods for Assessing Acute Systemic Toxicity of August 2001 as well as other NIH publications in this respect. Particular screening applications of this invention relate to the testing of pharmaceutical compounds in drug research. It is generally referred to the standard textbook "In vitro Methods in Pharmaceutical Research", Academic Press, 1997, and U.S. Pat. No. 5,030,015).

For use in pharmacological compound screening or as method to detect embryotoxic compounds in an high throughput in vitro system, the EBs can be manufactured using ES cells with an appropriate reporter gene (e.g. a fluorescent reporter like GFP) driven by an tissue-specific promoter (e.g. α-MHC for cardiomyocytes); see also the examples. After plating into 96-well plates (flat bottom, black; Falcon, Becton Dickinson), the EBs are challenged with the test compounds at different concentrations or with the diluents as control. Half of the medium is replaced with fresh medium and compound twice a week. After differentiation towards cardiomyocytes appears in the control EBs, the fluorescence in all EBs is measured using a fluorescence spectrophotometer (Tecan). The embryotoxic effect of the test compounds is calculated as percent of the controls, which are defined as 100%. Hence, the present invention also relates to a method for identifying and/or obtaining a drug for the amelioration or treatment of a disease or for determining the toxicity of a compound comprising:

(a) contacting a test sample comprising an embryoid body (EB) obtained by a method of the present invention or a differentiated cell or tissue thereof with a test substance to be screened; and
(b) determining a responsive change of the phenotype of said EB cell or tissue, wherein a responsive change compared to a control is indicative for a useful drug or for the toxicity of the compound.

Of course, the person skilled in the art will immediately recognize that the effect of the test substance on the EBs to be determined may include any responsive change of a phenotype of said EB or differentiated cell thereof. For example, said effect, i.e. phenotype includes but is not limited to a parameter selected from the group consisting of cell size, cell shape, cell viability, apoptotic cell death, protein synthesis, organization of actin/myosin filament, cell- or tissue-specific gene expression pattern and/or activation of genes expressed during early embryonic development.

Generally it can be referred to the standard textbook In vitro Methods in Pharmaceutical Research, Academic Press, 1997, and U.S. Pat. No. 5,030,015. Assessment of the activity of candidate compounds generally involves combining the EBs or differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change. The phenotypic changes effected by the test compound on the in vitro differentiated cell contacted with an agent can be assessed by any means known to one of skill in the art. In one embodiment the morphology is examined, for example (electron) microscopy is used to assess the (ultra)structure of the cells. Suitable parameters for evaluation include, but are not limited to the evaluation of gap junctions between contacting cells such as cardiomyocytes. In other embodiments, immunohistochemical or immunofluorescence techniques are used to assess the phenotype; see Example 4 and FIG. 6. In yet another embodiment, phenotypic changes are assessed by analysis expression of specific mRNA molecules expressed in the cells. Suitable assay systems include, but are not limited to RT-PCR, in situ hybridization, Northern analysis, or RNase protection assays. In a further embodiment the levels of polypeptides expressed in the differentiated cells are assayed. Specific, non-limiting examples of polypeptide assays of use include Western blot analysis, ELISA assay, or immunofluorescence. Alternatively, calcium transients are measured, as described infra.

The assay can also be used to screen the effect of an agent on the function of a cell, e.g., cardiomyocyte function. Any method known to one of skill in the art can be utilized to assess cardiac function. In one embodiment the beating rate of a cardiomyocyte is assayed to identify agents that increase or decrease beating. One method for assessing the beating rate is to observe beating under a microscope. Agents that can be screened in this manner include inotropic drugs, such as sympathomimetic agents. In one embodiment, cells contacted with the agent are compared with a control. Suitable controls include cells not contacted with the agent, or contacted with vehicle alone. Standard values can also be used as a control.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. It can be referred to A. Vickers (375-410) in In vitro Methods in Pharmaceutical Research, Academic Press, 1997) for further elaboration.

Effect of cell function can be assessed using any standard assay to observe phenotype or for example activity of cardiomyocytes, such as marker expression, receptor binding, contractile activity, or electrophysiology in cell culture. Pharmaceutical candidates can also be tested for their effect on contractile activity such as whether they increase or decrease the extent or frequency of contraction. Where an effect is observed, the concentration of the compound can be titrated to determine the median effective dose.

The assays may be simple "yes/no" assays to determine whether there is a responsive change compared to a control. The test compound or a plurality of test compounds can also be subjected to the test cell, preferably embryoid body in different concentrations or dilution series, preferably at doses that correspond to physiological levels of the corresponding type of test compounds. It is thus also possible to easy generate compound profiles in purpose similar to those described in WO00/34525. For example, two or more assays may be used and/or parameters may be assessed. Those assays/parameters can be performed/assessed in parallel or subsequently; or the results of one assay may be compared with the results of a corresponding assay performed elsewhere. Once the molecular profile of the test composition is determined, it can be compared to that of a chemical composition with predetermined biological activities or, preferably, to a library of molecular profiles of chemical compositions with predetermined biological activities. The outcome of such comparison provides information for one to predict the likelihood of whether the test composition has the potential of a drug or is toxic, what type of toxicity, and how toxic it would be as compared to the other known toxic compositions.

In a further embodiment, said method is performed on an array. Arrays for use in the assay of the present invention usually comprise a solid support and attached thereto or suspended thereon the in vitro differentiated cells. The use of planar microelectrode arrays for cultured cells and cell aggregates as biosensors is of particular interest. Such arrays generally consist of a substrate of glass, plastic or silicon over which a conductor, e.g. gold, platinum, indium-tin-oxide, iridium, etc., is deposited and patterned. An insulating layer, e.g., photoresist, polyimide, silicon dioxide, silicon nitride, etc., is deposited over the conducting electrodes and interconnects and then removed in regions over the electrodes to define the recording sites. Cells are cultured directly on this surface and contact the exposed conductor at the deinsulated recording sites. Depending on the size of the electrodes and the cells, recordings of electrical activity can be from a single cell or populations of cells including cell aggregates. Each electrode site is generally connected to the input of a high input impedance, low noise amplifier, with or without AC coupling capacitors, to allow amplification of the relatively small extracellular signals. Examples of such biosensors are described by Novak et al. IEEE Transactions on Biomedical Engineering BME-33(2) (1986), 196-202; Drodge et al., J. Neuroscience Methods 6 (1986), 1583-1592; Eggers et al., Vac. Sci. Technol. B8(6) (1990), 1392-1398; Martinoia et al., J. Neuroscience Methods 48 (1993), 115-121; Maeda et al., J. Neuroscience 15 (1995), 6834-6845; and Mohr et al. Sensors and Actuators B-Chemical 34 (1996), 265-269.

In one embodiment, the method of the present invention is preferably performed with a multi- or microelectrode array (MEA), such as those mentioned above. This assay system of the present invention is a particularly advantageous alternative for animal testing for cardiac affect analyses, which are usually quite time-consuming and expensive. Thus, the functional tissue assay system is particularly useful in drug development and toxicity testing of any compound a human or animal might get in contact with. Microelectrode arrays (MEAs) are devices which allow the multiple extracellular recording of action potential generation and propagation within, for example, ES cell-derived cardiomyocytes. This recordings resemble the well-known ECG as it is used by physicians. The matrix of the MEAs usually consists of 60 gold electrodes integrated into the bottom of a specially designed cell culture device. ES cell-derived embryoid bodies (EBs) can be cultured in such devices. After attachment and spreading on the surface, the cells of the EBs containing the cardiomyocytes get in contact with the electrodes. All outcoming extracellular action potentials can then be recorded synchroneously during both short- and long time observation experiments. The following analysis of frequencies and latencies with an appropriate program allows to reveal the fine "electrical map" of the beating clusters.

For example, electrophysiological properties prior, during and after adding the test compound to cardiac myocytes can be followed by recordings of extracellular field potentials with microelectrode arrays (MEA) consisting of, e.g., 60 substrate-integrated electrodes; see Banach et al. Am. J. Physiol. Heart Circ. Physiol. (2003), February 6, p S0363-6135. Multiple arrays of tungsten microelectrodes were used to record the concurrent responses of brain stem neurons that contribute to respiratory motor pattern generation; see Morris et al., Respir. Physiol. 121 (2000), 119-133.

As described in Example 4, embryoid bodies are used in the assays of the present invention to test the chemical composition; see also infra. The choice of the particular species from which the embryoid body is derived will typically reflect a balance of several factors. First, depending on the purpose of the study, one or more species may be of particular interest. For example, human embryoid bodies will be of particular interest for use with compositions being tested as potential human therapeutics but also for toxicological tests for substances including industrial chemicals, while equine, feline, bovine, porcine, caprine, canine, or sheep embryoid bodies may be of more interest for a potential veterinary therapeutic. Embryoid bodies of other species commonly used in preclinical testing, such as guinea pigs, mice, rat, rabbits, pigs, and dogs, are also preferred. Typically, embryoid bodies of these species will be used for "first pass" screening, or where detailed information on toxicity in humans is not needed, or where a result in a murine or other one of these laboratory species has been correlated to a known toxicity or other effect in humans. Furthermore, with respect to human therapeutics, regulatory agencies generally require animal data before human trials can begin; it will generally be desirable to use embryoid bodies of species which will be used in the preclinical animal studies. The results of testing in the embryoid bodies can then guide the researcher on the degree and type of toxicity to anticipate during the animal trials. Certain animal species are known in the art to be better models of human toxicity of different types than are others, and species also differ in their ability to metabolize drugs; see, e.g., Williams, Environ. Health Perspect. 22 (1978), 133-138; Duncan, Adv. Sci. 23 (1967), 537-541. Thus, the particular species preferred for use in a particular preclinical toxicity study may vary according to the intended use of the drug candidate. For example, a species which provide a suitable model for a drug intended to affect the reproductive system may not be as suitable a model for a drug intended to affect the nervous system. Criteria for selecting appropriate species for preclinical testing are well known in the art.

Once an embryoid body culture has been initiated, it can be contacted with a chemical composition. Conveniently, the chemical composition is in an aqueous solution, preferably in a solvent conventionally used in cell culture, for example DMSO, and is introduced to the culture medium; see also the examples. The introduction can be by any convenient means, but will usually be by means of a pipette, a micropipettor, or a syringe. In some applications, such as high throughput screening, the chemical compositions will be introduced by automated means, such as automated pipetting systems, which may be on robotic arms. Chemical compositions can also be introduced into the medium as in powder or solid forms, with or without pharmaceutical excipients, binders, and other materials commonly used in pharmaceutical compositions, or with other carriers which might be employed in the intended use. For example, chemical compositions intended for use as agricultural chemicals or as petrochemical agents can be introduced into the medium by themselves to test the toxicity of those chemicals or agents, or introduced in combination with other materials with which they might be used or which might be found in the environment, to determine if the combination of the chemicals or agents has a synergistic effect. Typically, the cultures will be shaken at least briefly after introduction of a chemical composition to ensure the composition is dispersed throughout the medium.

The time as which a chemical composition is added to the culture is within the discretion of the practitioner and will vary with the particular study objective. Conveniently, the chemical composition will be added as soon as the embryoid body develops from the stem cells, permitting the determination of the alteration in protein or gene expression on the development of all the tissues of the embryoid body. It may be of interest, however, to focus the study on the effect of the composition on a particular tissue type. As previously noted, individual tissues, such as muscle, nervous, and hepatic tissue, are known to develop at specific times after the embryoid body has formed. Addition of the chemical composition can therefore be staged to occur at the time the tissue of interest commences developing, or at a chosen time after commencement of that development, in order to observe the effect on altering gene or protein expression in the tissue of interest.

Different amounts of a chemical composition will be used to contact an embryoid body depending on the amount of information known about the toxicity of that composition, the purposes of the study, the time available, and the resources of the practitioner. A chemical composition can be administered at just one concentration, particularly where other studies or past work or field experience with the compound have indicated that a particular concentration is the one which is most commonly found in the body. More commonly, the chemical composition will be added in different concentrations to cultures of embryoid bodies run in parallel, so that the effects of the concentration differences on gene or protein expression and, hence, the differences in toxicity of the composition at different concentrations, can be assessed. Typically, for example, the chemical composition will be added at a normal or medium concentration, and bracketed by twofold or fivefold increases and decreases in concentration, depending on the degree of precision desired.

Where the composition is one of unknown toxicity, a preliminary study is conveniently first performed to determine the concentration ranges at which the composition will be tested. A variety of procedures for determining concentration dosages are known in the art. One common procedure, for example, is to determine the dosage at which the agent is directly toxic. The practitioner then reduces the dose by one half and performs a dosing study, typically by administering the agent of interest at fivefold or twofold dilutions of concentration to parallel cultures of cells of the type of interest. For environmental contaminants, the composition will usually also be tested at the concentration at which it is found in the environment. For agricultural chemicals, such as pesticides which leave residues on foodstuffs, the agent will usually be tested at the concentration at which the residue is found, although it will likely be tested at other concentrations as well. Thus, the dilution of test compounds can be done by making in separated tubes a series of dilution of 50 or 100 fold concentrated compounds in DMSO. One or two µl of each dilution are distributed in each well before cell suspension distribution.

Furthermore, the phenotype or characteristic of the EB and differentiated cell, respectively, may include any one or all of the following parameters that may be analyzed:
(i) $Na^+$ channels;
(ii) $Ca^{2+}/K^+$ channels;
(iii) $K^+$ channels;
(iv) amplitude and/or field potential duration (FDP);
(v) chronotrophy of cardiac cells or burst periods of neuronal cells;
(vi) arrhythmias, EAD-like phenomena;
(vii) pH value;
(viii) oxygen partial pressure ($pO_2$);
(ix) beating arrest;
(x) analysis of AV-dissociation contractility, NO-effects and/or morphological changes;
(xi) reporter gene expression or activity; or
(xii) marker gene expression.

In a preferred embodiment, the test sample comprises embryoid bodies (EBs) differentiated into cardiomyocytes, most preferably EBs that consist of functional cardiac tissue that beats autonomously and covers electrophysiological properties of atrial and ventricular cardiomyocytes, as well as of pacemaker cells.

In a particularly preferred embodiment of the method of the present invention said cell- or tissue-specific marker is selected from the group consisting of Troponin I, creatine kinase-MB or other cardiac-specific genes.

Assays and kits for the detection of such cell- and tissue-specific markers are well known in the art and commercially available, for example TropT and Cardiac T by Roche Diagnostics; apoptosis detection kits by a Promega, LDH-detection kit by Promega as well as by others; see also infra. In those embodiments, said embryoid body preferably consists of functional cardiac tissue comprising atrial and ventricular cardiomyocytes as well as pacemaker cells; see also supra.

As illustrated in the examples, the method of the present invention may comprise determining the fluorescence of said embryoid body, cell or tissue. Hence, in a particularly preferred embodiment of the method of the present invention, said embryoid body consists of functional cardiac tissue comprising atrial and ventricular cardiomyocytes as well as pacemaker cells, and said method comprises
(i) determining the amount of cardiac cells within the embryoid body by measurement of fluorescence;
(ii) measurement of cardiac-specific biomarkers; and
(iii) measurement of cell viability and/or apoptotic events.

Thus, the method of the present invention, in particular the time- and cost-saving provision of reproducible source of embryoid bodies, significantly improves embryonic stem cell tests (ESTs) that have been established so far; see for example Seiler et al., Altex 19 suppl. 1 (2002), 55-63, which refers to certain endpoints that are used to classify the toxic potential of chemicals, i.e. (i) the inhibition of the differentiation of ES cells into cardiomyocytes (ID50); (ii) degrees of viability of ES cells (IC50) in a MTT cytotoxicity test, supplemented with (iii) the corresponding viability test of 3T3 cells (IC503T3). A review on how to perform embryonic stem cell tests in the prior art including basics in cytotoxicity measurements such as ID50 and IC50 calculation is given in Genschow et al., ATLA 30 (2002), 151-176. For further information on toxicity tests based on embryonic stem cells it is referred to the scientific information service (SIS) on advanced alternative methods to animal experiments in biomedical sciences (ECVAM), which is a database of the European Commission and provides factual and evaluated information on advanced non-animal test development and validation for toxicology assessments.

Methods for determining the amount of cardiac cells within the embryoid body by measurement of fluorescence are well-known to the person skilled in the art; see also the examples. Furthermore, the measurement of cardiac-specific biomarkers is known to the person skilled in the art as well; see, for example, international application WO99/24571 and U.S. Pat. No. 6,657,104 and the references cited therein. The same applies to methods of measurement of cell viability and/or apoptotic events. For example, cell proliferation and cytotoxicity assays can be easily obtained by commercial suppliers such as Roche Diagnostics. For example, cellular DNA fragmentation ELISA assays, LDH cytotoxicity detection kits, MTT and XTT cell proliferation kits as well as WST-1 cell proliferation reagent are available from Roche Applied Science. Of course, other commercial suppliers as well as corresponding literature can be used and are well known in the art.

The advantages of this particular embodiment of screening assays of the present invention over conventional in vitro assays include
  Highly standardized cell culture model, homogeneous and reproducible production of EBs;
  Presence of atrial, ventricular, and pacemaker cells with normal physiological behavior (e.g. expression and regulation of ion channels);
  Entirely in vitro-based system, no requirement for laborious cell preparation;
  Time- and cost-saving Thus, in the various assays of the present invention compounds can be tested in accordance with methods described in DE 195 25 285 A1; Seiler et al., ALTEX 19 Suppl. 1 (2002), 55-63; Takahashi et al., Circulation 107 (2003), 1912-1916 and Schmidt et al., Int. J. Dev. Biol. 45 (2001), 421-429; the latter describing ES cell test (EST) used in a European Union validation study for screening of embryotoxic agents by determining concentration—dependently the differentiation of ES cells into cardiac and myogenic cells.

Preferred compound formulations for testing do not include additional components, such as preservatives, that have a significant effect on the overall formulation. Thus, preferred formulations consist essentially of a biologically active compound and a physiologically acceptable carrier, e.g. water, ethanol, DMSO, etc. However, if a compound is liquid without an excipient the formulation may consist essentially of the compound itself. Furthermore, a plurality of assays may be run in parallel with different compound concentrations to obtain a differential response to the various concentrations. As known in the art, determining the effective concentration of a compound typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection.

Compounds of interest encompass numerous chemical classes, though typically they are organic molecules; see also supra. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, nucleic acids, saccharides, fatty acids, steroids, purines, pyrimidines, derivatives, structural analogs or combinations thereof.

Compounds and candidate agents are obtained from a wide variety of sources including libraries of synthetic or natural compounds; see also supra. For example, numerous means are available for random and directed synthesis of a wide variety of organic compounds and biomolecules, including expression of randomized oligonucleotides and oligopeptides.

Alternatively, libraries of natural compounds in the form of bacterial, fungal, plant and animal extracts are available or readily produced. For example, inhibition of tumor-induced angiogenesis and matrix-metalloproteinase expression in confrontation cultures of embryoid bodies and tumor spheroids by plant ingredients used in traditional Chinese medicine has been described by Wartenberg et al. in Lab. Invest. 83 (2003), 87-98.

Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The compounds may also be included in a sample including fluids to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

Test compounds include all of the classes of molecules described above, and may further comprise samples of unknown content. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest compounds being assessed for potential therapeutic value, i.e. drug candidates.

The test compound may optionally be a combinatorial library for screening a plurality of compounds. Such a collection of test substances can have a diversity of about $10^3$ to about $10^5$ is successively reduced in running the method, optionally combined with others twice or more. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki et al., Bio/Technology 3 (1985), 1008-1012, allele-specific oligonucleotide (ASO) probe analysis (Conner et al., Proc. Natl. Acad. Sci. USA 80 (1983), 278), oligonucleotide ligation assays (OLAs) (Landegren et al., Science 241 (1988), 1077), and the like. Molecular techniques for DNA analysis have been reviewed (Landegren et al., Science 242 (1988), 229-237). Hence, the method of the present invention can also be used for transcriptional profiling of the in vitro differentiated cell; see, e.g., Ramalho-Santos et al., Science 298 (2002), 597-600; Tanaka et al., Genome Res. 12 (2002), 1921-1928.

The assay methods of the present invention can be in conventional laboratory format or adapted for high throughput. The term "high throughput" (HTS) refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired.

In another preferred embodiment, the method of the present invention comprises taking 2, 3, 4, 5, 7, 10 or more measurements, optionally at different positions within the array. Several test substances can be combined and either added simultaneously or sequentially to gain information about possible enhancing or quenching effects. Thus a further aspect of the invention relates to the method described previously, wherein said contacting step further includes contacting said test sample with at least one second test substance in the presence of said first test substance. Two or more substances tested in combination will provide information about their interaction in general. In one embodiment of the screening methods of the present invention a compound known to activate or inhibit disease process is added to the sample or culture medium.

Furthermore, the above-described methods can, of course, be combined with one or more steps of any of the above-described screening methods or other screening methods well known in the art. Methods for clinical compound discovery comprises for example ultrahigh-throughput screening (Sundberg, Curr. Opin. Biotechnol. 11 (2000), 47-53) for lead identification, and structure-based drug design (Verlinde and Hol, Structure 2 (1994), 577-587) and combinatorial chemistry (Salemme et al., Structure 15 (1997), 319-324) for lead optimization. Once a drug has been selected, the method can have the additional step of repeating the method used to perform rational drug design using the modified drug and to assess whether said modified drug displays better affinity according to for example interaction/energy analysis. The method of the present invention may be repeated one or more times such that the diversity of said collection of compounds is successively reduced.

Substances are metabolized after their in vivo administration in order to be eliminated either by excretion or by metabolism to one or more active or inactive metabolites (Meyer, J. Pharmacokinet. Biopharm. 24 (1996), 449-459). Thus, rather than using the actual compound or drug identified and obtained in accordance with the methods of the present invention a corresponding formulation as a pro-drug can be used which is converted into its active form in the patient by his/her metabolism. Precautionary measures that may be taken for the application of pro-drugs and drugs are described in the literature; see, for review, Ozama, J. Toxicol. Sci. 21 (1996), 323-329.

Furthermore, the present invention relates to the use of a compound identified, isolated and/or produced by any of these methods for the preparation of a composition for the treatment of disorders related to, for example damaged tissue or aberrant tissue or organ formation, heart insufficiency, etc.; see also supra. Preferably, the isolated compound or corresponding drug is useful for the treatment of a cardiomyopathy. As a method for treatment the identified substance or the composition containing it can be administered to a subject suffering from such a disorder. Compounds identified, isolated and/or produced by the method described above can also be used as lead compounds in drug discovery and preparation of drugs or prodrugs. This usually involves modifying the lead compound or a derivative thereof or an isolated compound as described hereinbefore such as modifying said substance to alter, eliminate and/or derivatize a portion thereof suspected causing toxicity, increasing bioavailability, solubility and/or half-life. The method may further comprise mixing the substance isolated or modified with a pharmaceutically acceptable carrier. The various steps recited above are generally known in the art. For example, computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, peptidomimetics and/or computer aided design of appropriate derivatives and analogues can be used, for example, according to the methods described above. Methods for the lead generation in drug discovery also include using proteins and detection methods such as mass spectrometry (Cheng et al. J. Am. Chem. Soc. 117 (1995), 8859-8860) and some nuclear magnetic resonance (NMR) methods (Fejzo et al., Chem. Biol. 6 (1999), 755-769; Lin et al., J. Org. Chem. 62 (1997), 8930-8931). They may also include or rely on quantitative structure-action relationship (QSAR) analyses (Kubinyi, J. Med. Chem. 41 (1993), 2553-2564, Kubinyi, Pharm. Unserer Zeit 23 (1994), 281-290) combinatorial biochemistry, classical chemistry and others (see, for example, Holzgrabe and Bechtold, Pharm. Acta Helv. 74 (2000), 149-155). Furthermore, examples of carriers and methods of formulation may be found in Remington's Pharmaceutical Sciences.

Once a drug has been selected in accordance with any one of the above-described methods of the present invention, the drug or a pro-drug thereof can be synthesized in a therapeutically effective amount. As used herein, the term "therapeutically effective amount" means the total amount of the drug or pro-drug that is sufficient to show a meaningful patient benefit, i.e., treatment, healing, prevention or amelioration of damaged tissue, or an increase in rate of treatment, healing, prevention or amelioration of such conditions. In addition or alternatively, in particular with respect to pre-clinical testing of the drug the term "therapeutically effective amount" includes the total amount of the drug or pro-drug that is sufficient to elicit a physiological response in a non-human animal test.

In one embodiment, the method of the invention further comprises mixing the substance isolated or modified with a pharmaceutically acceptable carrier. Examples of carriers and methods of formulation may be found in Remington's Pharmaceutical Sciences.

In addition, the present invention relates to an apparatus and array, respectively, for use in the methods and assays of the present invention described herein. For example, a cell-potential measurement apparatus having a plurality of microelectrodes and which may be used and/or adapted in accordance with the teaching of the present invention is described in European patent application EP 0 689 051 A3.

Furthermore, international application WO98/54294 describes an apparatus and method for monitoring cells and a method for monitoring changes in cells upon addition of an analyte to the cell's environment, comprising a device which includes an array of microelectrodes disposed in a cell culture chamber, upon which array a portion of cells adhere to the surfaces of the microelectrodes. The diameter of the cells are larger than the diameters of the microelectrodes. A voltage signal is applied across each of the microelectrodes and a reference electrode. Detection and monitoring of the signals resulting from the application of the voltage signal provides information regarding the electrical characteristics of the individual cells, including impedance (combined cell membrane capacitance and conductance), action potential parameters, cell membrane capacitance, cell membrane conductance, and cell/substrate seal resistance.

In a preferred embodiment, the present invention relates to the use of a fluorescence reader such as those described in the examples.

Further means and methods that may be implemented in accordance with the teaching of the present invention can be found in the literature, see for example Egert et al., Brain Res. Brain Res. Protoc. 2 (1998), 229-242; Duport et al., Biosens. Bioelectron. 14 (1999), 369-376 and German patent application DE 195 29 371 A1.

The present invention also relates to kit compositions containing specific reagents such as those described hereinbefore useful for conducting any one of the above described methods of the present invention, containing for example culture media components, selectable markers, reference samples, microarrays, vectors, probes, containers, multi- or pluripotent cells. Such a kit would typically comprise a compartmentalized carrier suitable to hold in close confinement at least one container. The carrier would further comprise reagents useful for performing said methods. The carrier may also contain a means for detection such as labeled enzyme substrates or the like. Hence, the present invention also relates to the use of cell containers, devices for agitation and/or culturing cells, culture media and components thereof, multi- or pluripotent cells, vectors, devices for recording fluorescence, and microarrays for use in a method of the invention described hereinbefore.

Hence, the means and methods of the present invention described hereinbefore can be used in a variety of applications including, but not limited to "loss of function" assays with ES cells containing homozygous mutations of specific genes, "gain of function" assays with ES cells overexpressing exogenous genes, developmental analysis of teratogenic/embryotoxic compounds in vitro, organ-specific analysis of toxic compounds, e.g., cardiotoxic or neurotoxic compounds, pharmacological assays and the establishment of model systems for pathological cell functions, and application of differentiation and growth factors for induction of selectively differentiated cells, which can be used as a source for tissue grafts; see for review, e.g., Guan et al., Altex 16 (1999), 135-141.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example, the public database "medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. A more complete understanding can be obtained by reference to the following specific examples which are provided herein for purposes of illustration only and are not intended to limit the scope of the invention. The contents of all cited references (including literature references, issued patents, published patent applications as cited throughout this application and manufacturer's specifications, instructions, etc.) are hereby expressly incorporated by reference; however, there is no admission that any document cited is indeed prior art as to the present invention.

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques concerning stem cell technology, the practitioner can refer to standard textbooks and reviews, for example Teratocarcinomas and embryonic stem cells: A practical approach (E. J. Robertson, ed., IRL Press Ltd. 1987); Guide to Techniques in Mouse Development (P. M. Wasserman et al., eds., Academic Press 1993); Embryonic Stem Cell Differentiation in Vitro (Wiles, Meth. Enzymol. 225 (1993), 900); Properties and uses of Embryonic Stem Cells: Prospects for Application to Human Biology and Gene Therapy (Rathjen et al., Reprod. Fertil. Dev. 10 (1998), 31). Differentiation of stem cells is reviewed in Robertson, Meth. Cell Biol. 75 (1997), 173; and Pedersen, Reprod. Fertil. Dev. 10 (1998), 31. Besides the sources for stem cells described already above further references are provided; see Evans and Kaufman, Nature 292 (1981), 154-156; Handyside et al., Roux's Arch. Dev. Biol., 196 (1987), 185-190; Flechon et al., J. Reprod. Fertil. Abstract Series 6 (1990), 25; Doetschman et al., Dev. Biol. 127 (1988), 224-227; Evans et al., Theriogenology 33 (1990), 125-128; Notarianni et al., J. Reprod. Fertil. Suppl., 43 (1991), 255-260; Giles et al., Biol. Reprod. 44 (Suppl. 1) (1991), 57; Strelchenko et al., Theriogenology 35 (1991), 274; Sukoyan et al., Mol. Reprod. Dev. 93 (1992), 418-431; Iannaccone et al., Dev. Biol. 163 (1994), 288-292.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (D. N. Glover ed., 1985); Oligonucleotide Synthesis (M. J. Gait ed., 1984); Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Gene Transfer Vectors for Mammalian Cells (Miller & Calos, eds.); Current Protocols in Molecular Biology and Short Protocols in Molecular Biology, 3rd Edition (F. M. Ausubel et al., eds.); and Recombinant DNA Methodology (R. Wu ed., Academic Press). Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.); Immobilized Cells And Enzymes (IRL Press, 1986); B. Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251). Other observations about the media and their impact on the culture environment have been made by Marshall McLuhan and Fred Allen.

EXAMPLES

Example 1

Generation of "Embryoid Bodies" (EBs) from High Density Cell Suspensions and Differentiation of Cardiac Cells (FIG. 1, Protocol 1)

Mouse embryonic stem cells (ES cells, clone D3, ATCC CRL 1934) were stably transfected with the pαMHC-GFP vector containing the gene of the green fluorescent protein under control of the cardiac α-myosin heavy chain (α-MHC) promotor. To obtain this vector, a 5.5 kb fragment containing the promotor region of the mouse (α-myosin heavy chain gene (Genbank 471441) was introduced into the polylinker of the pEGFP-1 vector (Clontech Laboratories).

ES cells were cultured on 10 cm petri dishes (Falcon, Becton Dickinson) at a density of $1.4 \times 10^6$ in DMEM (Gibco, Invitrogen) supplemented with 15% FCS (Gibco, invitrogen, batch controlled) and $1 \times 10^3$ U/ml LIF (Chemicon) on a layer of feeder cells (inactivated mouse embryonic fibroblasts, prepared according standard protocols; see also description of the invention above). Cells were incubated at 37° C., 7% $CO_2$ and 95% humidity. Cells were split every second day by trypsinizing them to single cell suspension and seeding $1.4 \times 10^6$ on a fresh 10 cm dish coated with feeder cells.

ES cells from one ore more petri dishes were trypsinised to obtain a single cell suspension and collected by centrifugation (800 g for 5 min). Cells were resuspended to a density of $2 \times 10^6$ cells/ml in Iscove's Modified Dulbecco's Medium (IMDM, Invitrogen) supplemented with 20% (v/v) fetal bovine serum (FBS, Invitrogen, batch controlled).

Figure 4:
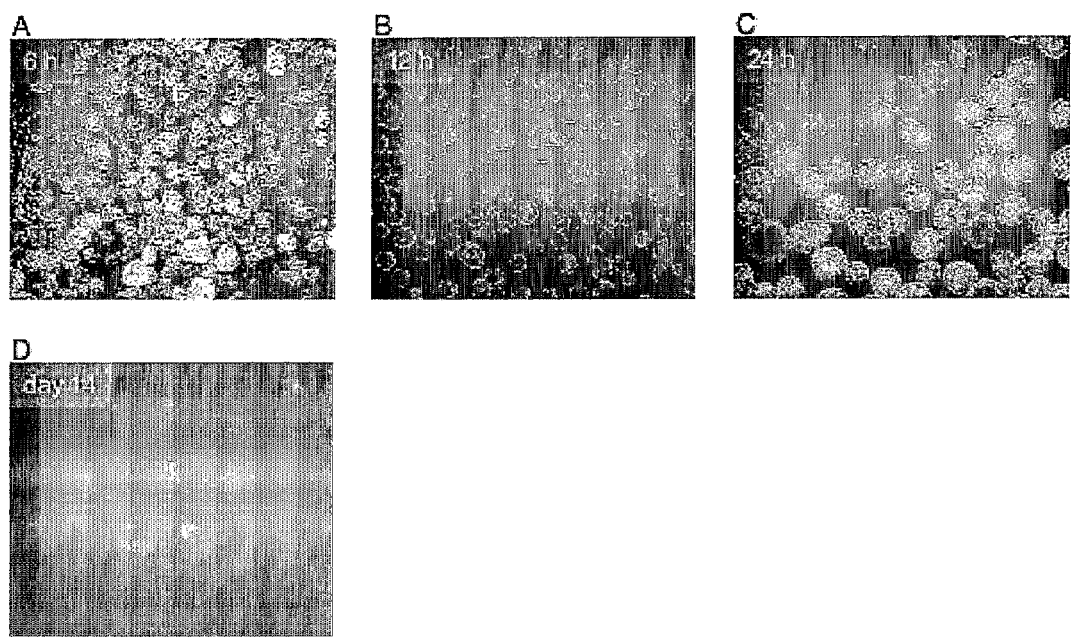
FIG. 4: Generation of embryoid bodies (EBs) and differentiation towards cardiac tissue. EBs were generated as described in Example 1, and microphotographs were taken after 6, 12 and 24 hours (phase contrast, total magnification 50×) and on day 14 (fluorescence, total magnification 50×). Light-grey areas on day 14 represent cardiac cells.

To generate EBs, ES cells were cultured in suspension at a density of $2 \times 10^6$ cells/ml in a 6 cm petri dish (Greiner, Darmstadt, Germany) in 4 ml IMDM with 20% FCS (Invitrogen, Karlsruhe, Germany) at 37° C., 5% $CO_2$, 95% humidity on a rocking table (GFL 3006, GFL, Braunschweig, Germany) at 50 rpm for 6 hours. After 6 hours the suspension was diluted 1:10 with IMDM with 20% FCS and incubated for additional 12-16, preferably to a total of (steps (a) and (b)) 18 hours in T25 cell culture flasks (Falcon, Becton Dickinson, Heidelberg, Germany) on the rocking table at 37° C., 5% $CO_2$, 95% humidity. On the next day, EB suspension was transferred to a COPAS select particle sorter (Union Biometrica, Geel, Belgium) and single EBs were sorted into the wells of 96-well U-shaped microtiter plates (Greiner) according to the manufacturer's instructions. EBs were cultured in 200 μl IMDM 20% FCS per well and incubated at 37° C., 5% $CO_2$, 95% humidity. On day 5 and 10, the medium was replaced by fresh medium. On day 14, fluorescent areas representing cardiac cells were detected by fluorescence microscopy using a Zeiss Axiovert 200 M with a 10× Achroplan objective, a HQ-filterset for GFP (AF Analysentechnik, Tu ibingen, Germany) and a Sensicam 12 bit cooled imaging system (PCO Imaging, Kelheim, Germany). Microphotographs of EBs at different stages of culture are shown in FIG. 4. Total magnification is indicated in the figure legend.

Example 2

Generation of "Embryoid Bodies" (EBs) from Low Density Cell Suspensions and Differentiation of Cardiac Cells (FIG. 1, Protocol 2)

ES cells were cultured as describe in Example 1. To generate EBs, ES cells were cultured in suspension at a density of $0.2 \times 10^6$ cells/ml in a 10 cm petri dish (Greiner, Darmstadt, Germany) in 10 ml IMDM with 20% FCS (Invitrogen, Karlsruhe, Germany) at 37° C., 5% $CO_2$, 95% humidity on a rocking table (GFL 3006, GFL, Braunschweig, Germany) at 50 rpm for 48 hours. On day 2, 100-2000 EBs were transferred to 10 cm bacterial dishes (Greiner) into a volume of 10 ml IMDM 20% FCS and incubated at 37° C., 5% $CO_2$, 95% humidity, either with or without agitation. On day 5 and 7, or every other day for high density suspensions such as 2000 EBs/10 ml, the medium was replaced by 10 ml of fresh medium. On day 14, fluorescent areas representing cardiac cells were detected by fluorescence mircoscopy using a Zeiss Axiovert 200 M with a 10× Achroplan objective, a HQ-filterset for GFP (AF Analysentechnik, Tübingen, Germany) and a Sensicam 12 bit cooled imaging system (PCO Imaging, Kelheim, Germany).

Example 3

Figure 5:
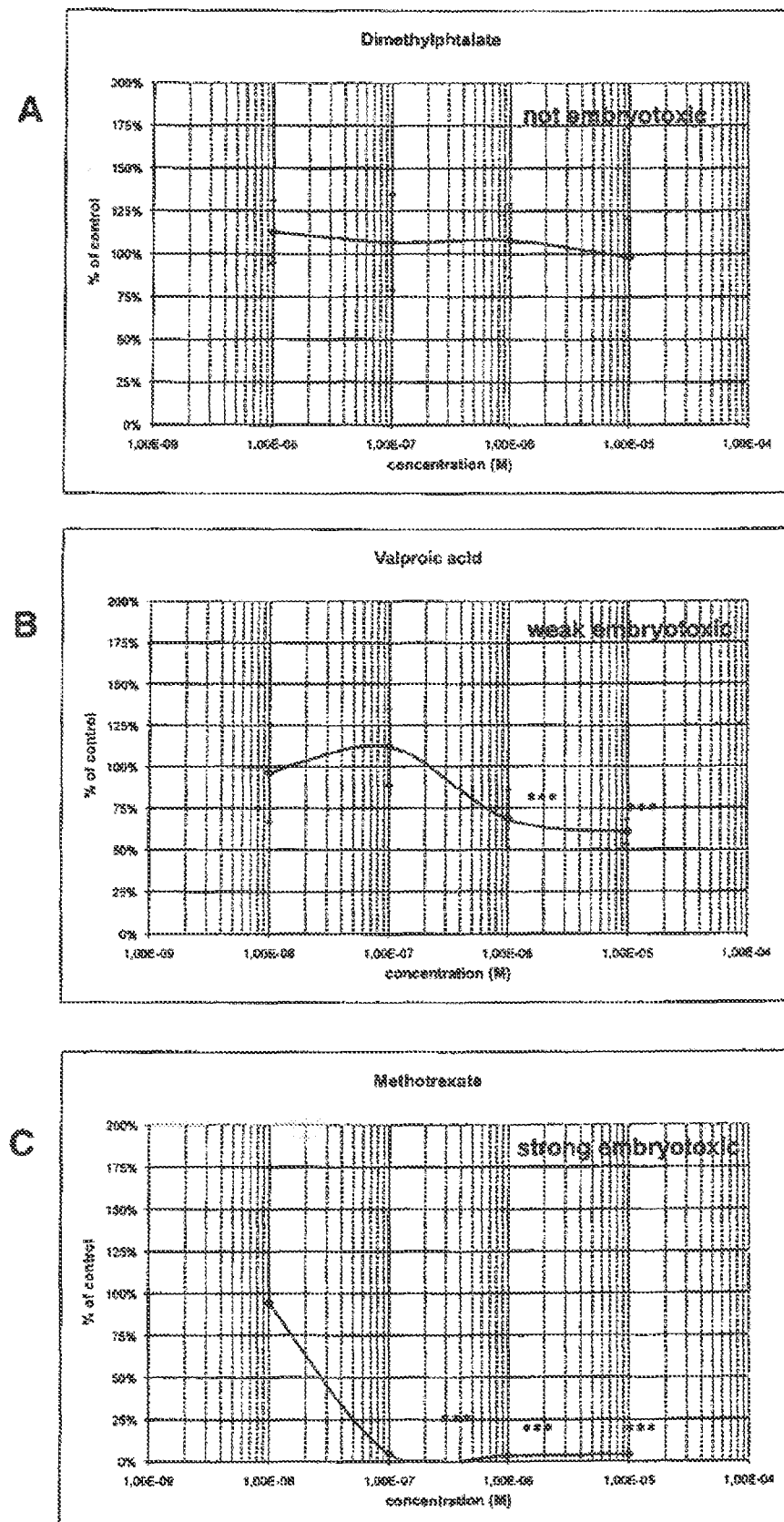
FIG. 5: Effect of different test compounds on differentiation capacity of EBs. EBs were generated and treated with test compounds with known embryotoxic potential as indicated in the figure. The concentrations of the test compounds were $10^{-8}$, $10^{-7}$, $10^{-6}$ and $10^{-5}$ M. On day 14, fluorescence intensity representing cardiac differentiation was measured and calculated as described in Example 3.

Effect of Embryotoxic Compounds on Differentiation Capacity of EBs towards Cardiomyocytes EBs were generated as described in Example 1. At day 1, 30 EBs were transferred to each well of a bacteriological 6-well plate (Greiner) into a volume of 3 ml IMDM 20% FCS, and test compounds with known embryotoxic potential were added at different concentrations as indicated in the figures (solvent: DMSO, final concentration of DMSO: 0.1%). Test compounds were chosen from a list of compounds recommended for a validation study on in vitro embryotoxicity tests by the European Center for the Validation of Alternative Methods (ECVAM) (see Brown, N A 2002; ATLA 30, 177-198). Each compound concentration was tested in triplicate in three individual experiments. EBs were cultured at 37° C., 5% $CO_2$, 95% humidity. On day 5, cultures were fed with 2 ml of fresh medium, and fresh test compounds were added. On day 14, EBs on each plate were counted, lysed in lysis buffer (20 mM Tris-HCl/0.5% TritonX 100) and fluorescence intensity was measured using a Tecan Safire®E (Tecan, Crailsheim, Germany) at a wavelength of 476/508 nm. Because not all EBs introduced into the test survive the procedure, the values were normalized to a supposed number of 100 EBs. Normalized values were then expressed as percent of control values (0.1% DMSO only). Compounds were judged as embryotoxic, if a significant alteration in differentiation was seen (Student's t-test). FIG. 5 shows the effects of 3 different test compounds, namely dimethylphtalate (non-embryotoxic), valproic acid (weak embryotoxic) and methotrexate (strong embryotoxic). *=p<0.05; **=p<0.01; *=p<0.002.

Example 4

Identification of Cardiotoxic Compounds

EBs were generated as described in Example 1. On day 5, 5 EBs were transferred into each well of a 24-well tissue culture plate (Falcon, Becton Dickinson) into 2 ml of IMDM 20% FCS and incubated at 37° C., 5% $CO_2$, 95% humidity. Half of the medium was replaced by fresh medium at day 10. At day 14, EBs were evaluated for cardiac differentiatation by fluorescence microscopy, and fluorescence microphotographs of EBs with fluorescent areas were taken using a Zeiss Axiovert 200 M with a 10× Achroplan objective, a HQ-filter-set for GFP (AF Analysentechnik) and a Sensicam 12 bit cooled imaging system (PCO Imaging). Cardiotoxic compounds were added at different concentrations as indicated in FIG. 6 (solvent: DMSO, final concentration of DMSO: 0.1%), 0.1% DMSO was used as a negative control. EBs were incubated at 37° C., 5% $CO_2$, 95% humidity additional 3 days. After 48 hours and 72 hours of incubation with the test compounds, fluorescence photomicrographs were taken, and the fluorescent areas were calculated using AnalySIS software (Soft Imaging Systems, Münster, Germany). Values obtained after treatment with the test compounds were compared with the values obtained before the treatment. FIG. 6 shows the effects of 3 different compounds, namely dexamethasone (non cardiotoxic), doxorubicine (cardiotoxic) and emetine (cardiotoxic) on ES cell-derived cardiomyocytes during 72 hours.

The invention claimed is:

1. A method for producing embryoid bodies (EBs) from pluripotent cells comprising
   (i) obtaining a liquid single cell suspension culture of pluripotent cells;
   (ii) collecting and suspending the cells in a container to a density of about $0.5 \times 10^6$ to $5 \times 10^6$ cells/ml;
   (iii) rocking the container containing the liquid single cell suspension culture thereby generating cell aggregates; and
   (iv) diluting the suspension, and further rocking a container containing the suspension until formation of EBs;
   wherein the final concentration of EBs in the suspension culture is about 500 EBs/ml;
   wherein the pluripotent cells are selected from the group consisting of embryonic stem (ES) cells, primordial germ (EG) cells and non-embryonic pluripotent stem cells.

2. The method of claim 1, wherein prior to step (i) the cells are cultured on embryonic mouse fibroblasts (feeder cells).

3. The method of claim 1 or 2, wherein said pluripotent cells are embryonic stem (ES) cells.

4. The method of claim 3, wherein said cells are obtained from a, murine ES cell line.

5. The method of claim 1, wherein the culture medium in any or all of the steps is Iscove's Modified Dulbecco's Media (IMDM) and 20% FCS.

6. The method of claim 1, wherein the culture conditions in any or all of steps (i) through (iii) comprise 37° C., 5% $CO_2$ and 95% humidity.

7. The method of claim 1, wherein said culture of pluripotent cells has a concentration of about $1 \times 10^6$ to $5 \times 10^6$ cells/ml.

8. The method of claim 1, wherein the suspension in step (iii) is cultured for about 6 hours.

9. The method of claim 1, wherein the suspension is cultured for about 16 to 20 hours.

10. The method of any one of claims 1, 8 and 9, wherein the suspension in step (iv) is cultured in T25 flasks.

11. The method of claim 1, wherein said dilution in step (iv) is 1:10.

12. The method of claim 1, further comprising diluting the cell aggregates to the desired final concentration.

13. The method of claim 1, further comprising culturing the EBs under conditions allowing differentiation of the EBs into cardiomyocytes.

14. The method of claim 13, further comprising selection of cardiomyocytes by use of one or more selectable markers or agents or both.

15. The method of claim 14, wherein said cell is genetically engineered.

16. The method of any one of claims 14 and 15, wherein said cell comprises a selectable marker or a reporter gene or both.

17. The method of claim 16, wherein said cell comprises a selectable marker gene operably linked to a cell type-specific regulatory sequence.

18. The method of claim 17, wherein said selectable marker confers resistance to puromycin.

19. The method of claim 17, wherein said cell type-specific regulatory sequence is atrial- or ventricular-specific.

20. The method of claim 19, wherein said regulatory sequence is a cardiac-specific regulatory sequence selected from the group consisting of the promoters of alpha-myosin heavy charin (alpha-MHC) and ventricular myosin light chain 2 (MLC2v).

21. The method of claim 16, wherein said cell comprises a reporter gene operably linked to a cell type-specific regulatory sequence.

22. The method of claim 21, wherein said cell type-specific regulatory sequence of the reporter gene is the same as said cell type-specific regulatory sequence of the marker gene.

23. The method of claim 22, wherein said reporter is enhanced green fluorescent protein (EGFP).

24. The method of claim 21, wherein said cell type-specific regulatory sequence is atrial- or ventricular-specific.

25. The method of claim 16, wherein said marker gene and said reporter gene are contained on the same recombinant nucleic acid molecule.

26. The method of claim 25, wherein said marker gene and said reporter gene are contained on the same cistron.

27. A method for producing embryoid bodies (EBs) from pluripotent cells comprising
   (i) obtaining a liquid single cell suspension culture of pluripotent cells;

(ii) collecting and suspending the cells in a container to a density of about $0.1\times10^6$ to $1\times10^6$ cells/ml;

(iii) rocking the container containing the liquid single cell suspension culture thereby generating cell aggregates; and (iv) rocking the container containing the suspension until formation of EBs;

wherein the pluripotent cells are selected from the group consisting of embryonic stem (ES) cells, primordial germ (EG) cells and non-embryonic pluripotent stem cells, and wherein a 10 ml aliquot of a suspension in (ii) comprising $0.2\times10^6$ pluripotent cells yields sufficient EBs to seed six 20 ml suspensions each comprising 1000 EBs.

28. The method of claim 27, wherein prior to step (iii) the cells are cultured on embryonic mouse fibroblasts (feeder cells).

29. The method of claim 27 or 28, wherein said pluripotent cells are embryonic stem (ES) cells.

30. The method of claim 29, wherein said cells are obtained from a murine ES cell line.

31. The method of claim 27, wherein the culture medium in any or all of the steps is Iscove's Modified Dulbecco's Media (IMDM) and 20% FCS.

32. The method of claim 27, wherein the culture conditions in any or all of steps (i) through (iv) comprise 37° C., 5% $CO_2$ and 95% humidity.

33. The method of claim 27, wherein said culture of pluripotent cells has a concentration of about $0.1\times10^6$ to $0.5\times10^6$ cells/ml.

34. The method of claim 27, wherein the suspension is cultured for about 48 hours.

35. The method of claim 27, further comprising culturing the EBs under conditions allowing differentiation of the EBs into cardiomyocytes.

36. The method of claim 35, further comprising selection of cardiomyocytes by use or one or more selectable markers or agents or both.

37. The method of claim 36, wherein said cell is genetically engineered.

38. The method of claim 36 or 37, wherein said cells comprises a selectable marker or a reporter gene or both.

39. The method of claim 38, wherein said cell comprises a selectable marker gene operably linked to a cell type-specific regulatory sequence.

40. The method of claim 39, wherein said selectable marker confers resistance to puromycin.

41. The method of claim 39, wherein said cell type-specific regulatory sequence is atrial- or ventricular-specific.

42. The method of claim 41, wherein said regulatory sequence is a cardiac-specific regulatory sequence selected from the group consisting of the promoters of alpha-myosin heavy chain (alpha-MHC) and ventricular myosin light chain 2 (MLC2v).

43. The method of claim 38, wherein said cell comprises a reporter gene operably linked to a cell type-specific regulatory sequence.

44. The method of claim 43, wherein said cell type-specific regulatory sequence of the reporter gene is the same as said cell type-specific regulatory sequence of the marker gene.

45. The method of claim 44, wherein said reporter is enhanced green fluorescent protein (EGFP).

46. The method of claim 43, wherein said cell type-specific regulatory sequence is atrial- or ventricular-specific.

47. The method of claim 38, wherein said marker gene and said reporter gene are contained on the same recombinant nucleic acid molecule.

48. The method of claim 37, wherein said marker gene and said reporter gene are contained on the same cistron.

* * * * *